(12) United States Patent
Filipe et al.

(10) Patent No.: US 11,692,215 B2
(45) Date of Patent: Jul. 4, 2023

(54) NUCLEIC ACID CLEAVING ENZYME-BASED BIOSENSOR AND METHODS OF USE THEREOF

(71) Applicant: McMaster University, Hamilton (CA)

(72) Inventors: Carlos Filipe, Ancaster (CA); Yingfu Li, Dundas (CA); Sahar Esmaeili Samani, Hamilton (CA); Dingran Chang, Toronto (CA); Erin M. McConnell, Hamilton (CA); Meghan Rothenbroker, Aurora (CA)

(73) Assignee: McMaster University, Hamilton (CA)

( * ) Notice: Subject to any disclaimer, the term of this patent is extended or adjusted under 35 U.S.C. 154(b) by 56 days.

(21) Appl. No.: 17/180,337

(22) Filed: Feb. 19, 2021

(65) Prior Publication Data

US 2021/0262013 A1 Aug. 26, 2021

Related U.S. Application Data

(60) Provisional application No. 62/979,703, filed on Feb. 21, 2020.

(51) Int. Cl.
 *C12Q 1/6825* (2018.01)
 *C12Q 1/6823* (2018.01)

(52) U.S. Cl.
 CPC ......... *C12Q 1/6823* (2013.01); *C12Q 1/6825* (2013.01)

(58) Field of Classification Search
 CPC ...... C12Q 1/6823; C12Q 1/6825; C12Q 1/34; C12Q 2521/301; C12Q 2521/327; C12Q 2521/337; C12Q 2521/345; C12Q 2527/127; C12Q 2563/107; G01N 33/54373
 See application file for complete search history.

(56) References Cited

U.S. PATENT DOCUMENTS

| | | | |
|---|---|---|---|
| 2007/0111222 A1* | 5/2007 | Chasin | C12Q 1/37 514/1.2 |
| 2016/0047826 A1 | 2/2016 | Li et al. | |
| 2017/0219573 A1* | 8/2017 | Needham | G01N 33/54386 |
| 2018/0143191 A1* | 5/2018 | Van Rossum | G01N 33/558 |

FOREIGN PATENT DOCUMENTS

WO WO-2007109500 A1 * 9/2007 ........... C12Q 1/6834

OTHER PUBLICATIONS

Chen et al. Sensors and Actuators B; 2018; 254: 214-221. (Year: 2018).*
Ali et al. Scientific Reports; 2017; vol. 7, Article No. 12335: p. 1-10. (Year: 2017).*
Wang et al. Colloids and Surfaces B: Biointerfaces; 2018; 169: 305-312. (Year: 2018).*
Tram et al. Chem. Int. Ed.; 2014; 53: 12799-12802. (Year: 2014).*
Li et al. Anal. Chem.; 2015; 87,:4829-4835. (Year: 2015).*
Preechakasedkit et al. Biosensors and Bioelectronics; 2018; 102: 27-32. (Year: 2018).*
Hughes et al. MRS Adv. 2018; 3(26): 1491-1496. (Year: 2018).*
Wu et al. ACSNANO: 2010; vol. 4; No. 10: 5897-5904. (Year: 2010).*
Anfossi et al. Analytical and Bioanalytical Chemistry; 2019; 411:1905-1913. (Year: 2018).*
Lu et al. Analytical Chemistry; 2010; 82: 329-335. (Year: 2010).*
Carmi et al. In vitro selection of self-cleaving DNAs. Chemistry & Biology, published Dec. 1996, vol. 3(12), pp. 1039-1046.
Wang et al. Characterization of deoxyribozymes with site-specifc oxidative cleavage activity against DNA obtained by in vitro selection. Organic & Biomolecular Chemistry, published Jan. 19, 2016, vol. 14(7), pp. 2347-2351.
Robertson and Joyce. Selection in vitro of an RNA enzyme that specifically cleaves single-stranded DNA. Nature, published Mar. 29, 1990, vol. 344, pp. 467-468.
Giljohann and Mirkin. Drivers of biodiagnostic development. Nature, published Nov. 26, 2009, vol. 462, pp. 461-464.
Yager et al. Microfluidic diagnostic technologies for global public health. Nature, published Jul. 27, 2006, vol. 442, pp. 412-418.
Parolo and Merkoçi. Paper-based nanobiosensors for diagnostics. Chemical Society Reviews, published Oct. 2, 2012, vol. 42(2), pp. 450-457.
Fire and Xu. Rolling replication of short DNA circles. Proceedings of the National Academy of Sciences of the United States of America, published May 9, 1995, vol. 92, pp. 4641-4645.
Ali et al. Rolling circle amplification: a versatile tool for chemical biology, materials science and medicine. Chemical Society Reviews, published Mar. 18, 2014, vol. 43, pp. 3324-3341.
Liu et al. Biosensing by Tandem Reactions of Structure Switching, Nucleolytic Digestion, and DNA Amplification of a DNA Assembly. Angewandte Chemie, published Jun. 26, 2015, vol. 127, pp. 9773-9777.
Liu et al. Programming a topologically constrained DNA nanostructure into a sensor. Nature Communications, published Jun. 23, 2016, vol. 7, pp. 1-7.
Liu et al. A DNAzyme Feedback Amplification Strategy for Biosensing. Angewandte Chemie International Edition, published Mar. 28, 2017, vol. 56, pp. 6142-6146.
Liu et al. Self-Assembled Functional DNA Superstructures as High-Density and Versatile Recognition Elements for Printed Paper Sensors. Angewandte Chemie International Edition, published Jul. 24, 2018, vol. 130, pp. 12620-12623 (same as vol. 57, pp. 12440-12443 of the international edition).
Breaker. DNA Enzymes. Nature Biotechnology, published May 1997, vol. 15, pp. 427-431.
Schlosser and Li. Biologically Inspired Synthetic Enzymes Made from DNA. Chemistry & Biology, published Mar. 27, 2009, vol. 16, pp. 311-322.

(Continued)

*Primary Examiner* — Narayan K Bhat
(74) *Attorney, Agent, or Firm* — Melanie Szweras; Herman Cheung; Bereskin & Parr LLP/ S.E.N.C.R.L., s.r.l.

(57) ABSTRACT

This disclosure relates to biosensors, and in particular, biosensors based on nucleic acid cleaving enzymes such as ribonucleotide-cleaving DNAzymes for the detection of analytes, and methods of use.

19 Claims, 9 Drawing Sheets

Specification includes a Sequence Listing.

(56) References Cited

OTHER PUBLICATIONS

Silverman. Catalytic DNA: Scope, Applications, and Biochemistry of Deoxyribozymes. Trends in Biochemical Sciences, published Jul. 1, 2016, vol. 41, pp. 595-609.
Liu et al. Discovery and Biosensing Applications of Diverse RNA-Cleaving DNAzymes. Accounts of Chemical Research, published Aug. 14, 2017, vol. 50, pp. 2273-2283.
Morrison et al. DNAzymes: Selected for Applications. Small Methods, first published Jan. 25, 2018, vol. 2, pp. 1700319 (12 pages).
Ellington and Szostak. In vitro selection of RNA molecules that bind specific ligands. Nature, published Aug. 30, 1990, vol. 346, pp. 818-822.
Tuerk and Gold. Systematic Evolution of Ligands by Exponential Enrichment: RNA Ligands to Bacteriophage T4 DNA Polymerase. Science, published Aug. 3, 1990, vol. 249, pp. 505-510.
Navani and Li. Nucleic acid aptamers and enzymes as sensors. Current Opinion in Chemical Biology, published Jun. 1, 2006, vol. 10, pp. 272-281.
Liu et al. Functional Nucleic Acid Sensors. Chemical Reviews, published Mar. 20, 2009, vol. 109, pp. 1948-1998.
Xiang and Lu. Using personal glucose meters and functional DNA sensors to quantify a variety of analytical targets. Nature Chemistry, published Jul. 24, 2011, vol. 3, pp. 697-703.
Tram et al. Translating Bacterial Detection by DNAzymes into a Litmus Test. Angewandte Chemie, published Nov. 14, 2014, vol. 126, pp. 13013-13016.
Zhang et al. In vitro selection of RNA-cleaving DNAzymes for bacterial detection. Methods, published Aug. 15, 2016, vol. 106, pp. 66-75.
Li and Lu. A Highly Sensitive and Selective Catalytic DNA Biosensor for Lead Ions. Journal of American Chemical Society, published Oct. 4, 2000, vol. 122, pp. 10466-10467.
Hwang et al. Photocaged DNAzymes as a General Method for Sensing Metal Ions in Living Cells. Angewandte Chemie International Edition, published Oct. 14, 2014, vol. 53, pp. 13798-13802.
Huang and Liu. Sensing Parts-per-Trillion Cd2+, Hg2+, and Pb2+ Collectively and Individually Using Phosphorothioate DNAzymes Analytical Chemistry, published May 22, 2014, vol. 86, pp. 5999-6005.
He et al. Highly Specific Recognition of Breast Tumors by an RNA-Cleaving Fluorogenic DNAzyme Probe. Analytical Chemistry, published Jan. 6, 2015, vol. 87, pp. 569-577.
Shen et al. A Catalytic DNA Activated by a Specific Strain of Bacterial Pathogen. Angewandte Chemie, published Feb. 12, 2016, vol. 128, pp. 2477-2480.
Ali et al. Fluorogenic DNAzyme Probe as Bacterial Indicators. Angewandte Chemie, published Mar. 15, 2011, vol. 123, pp. 3835-3838.
Aguirre et al. A Sensitive DNA Enzyme-Based Fluorescent Assay for Bacterial Detection. Biomolecules, published Aug. 20, 2013, vol. 3, pp. 563-577.
Chang et al. Detection of DNA Amplicons of Polymerase Chain Reaction Using Litmus Test. Scientific Reports, published online Jun. 8, 2017, vol. 7, pp. 1-8.
Deen. Drag, particles, and porous media. Introduction to Chemical Engineering Fluid Mechanics, Cambridge University Press, published Aug. 14, 2016, pp. 54-57.
Liu et al. Graphene-DNAzyme-based fluorescent biosensor for *Escherichia coli* detection. MRS Communications, published May 21, 2018, vol. 8(3), pp. 687-694.
Ali et al. A Printed Multicomponent Paper Sensor for Bacterial Detection. Scientific Reports, published online Sep. 26, 2017, vol. 7, Article 12335, pp. 1-10.
Dua et al. Cell-SELEX Based Identification of an RNA Aptamer for *Escherichia coli* and Its Use in Various Detection Formats. Molecules and Cells, published Nov. 18, 2016, vol. 39, pp. 807-813.
Wu et al. An Aptamer-Based Biosensor for Colorimetric Detection of *Escherichia coli* O157:H7. PLoS One, published Nov. 7, 2012, vol. 7(11), pp. 1-9.
Yu et al. Whole-bacterium SELEX of DNA aptamers for rapid detection of *E. coli* O157:H7 using a QCM sensor. Journal of Biotechnology, published Jan. 20, 2018, vol. 266, pp. 39-49.
Meng et al. Polymerase chain reaction for detecting *Escherichia coli* O157-H7. International Journal of Food Microbiology, published Sep. 1996, vol. 32, pp. 103-113.
Ibekwe et al. Multiplex Fluorogenic Real-Time PCR for Detection and Quantification of *Escherichia coli* O157:H7 in Dairy Wastewater Wetlands. Applied and Environmental Microbiology, published Oct. 1, 2002, vol. 68(10), pp. 4853-4862.
Waswa et al. Direct detection of *E. coli* O157:H7 in selected food systems by a surface plasmon resonance biosensor. LWT—Food Science and Technology, published Mar. 2007, vol. 40(2), pp. 187-192.
Adanyi et al. Development in new immunosensors for determination of contaminants in food. Current Applied Physics, published Feb. 2006, pp. 279-286.
Strachan and Ogden. A sensitive microsphere coagulation ELISA for *Escherichia coli* O157:H7 using Russell's viper venom. FEMS Microbiology Letters, published May 1, 2000, vol. 186, pp. 79-84.
Thakur et al. Rapid detection of single *E. coli* bacteria using a graphene-based field-effect transistor device. Biosensors and Bioelectronics, published Jul. 1, 2018, vol. 110, pp. 16-22.
Ali et al. A simple DNAzyme-based fluorescent assay for Klebsiella pneumoniae. ChemBioChem, published Apr. 1, 2019, vol. 20, pp. 906-910.
Manochehry et al. Colorimetric Detection of Uranyl Using a Litmus Test. Frontiers in Chemistry, published Aug. 4, 2018, vol. 6, Article 332, pp. 1-10.
Li et al. In vitro selection and characterization of a highly efficient Zn(II)-dependent RNA-cleaving deozyribozyme. Nucleic Acids Research, published Jan. 15, 2000, vol. 28(2), pp. 481-488.
Liu et al. Assemblage of Signaling DNA Enzymes with Intriguing Metal-Ion Specificities and pH Dependences. Journal of the American Chemical Society, published May 20, 2003, vol. 125, pp. 7539-7545.
Brown et al. A Lead-Dependent DNAzyme with a Two-Step Mechanism. Biochemistry, published May 23, 2003, vol. 42, pp. 7152-7161.
Torabi et al. In vitro selection of a sodium-specific DNAzyme and its application in intracellular sensing. Proceedings of the National Academy of Sciences of the United States of America, published May 12, 2015, vol. 112, pp. 5903-5908.
Tram et al. An efficient Catalytic DNA that Cleaves L-RNA, PLoS One, e0126402, published May 6, 2015, pp. 1-14.
Saran and Liu. A Silver DNAzyme. Analytical Chemistry, published Apr. 5, 2016, vol. 88, pp. 4014-4020.

\* cited by examiner

FIG. 1A
FIG. 1B
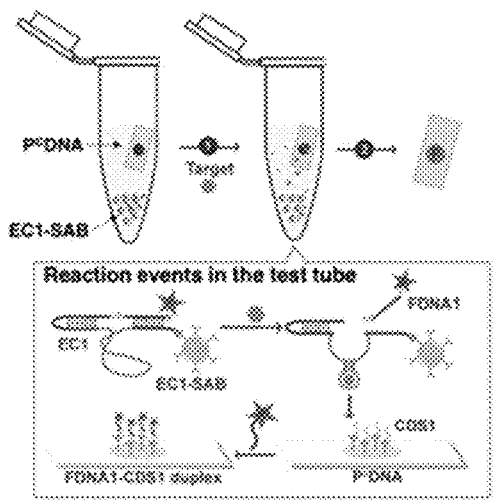
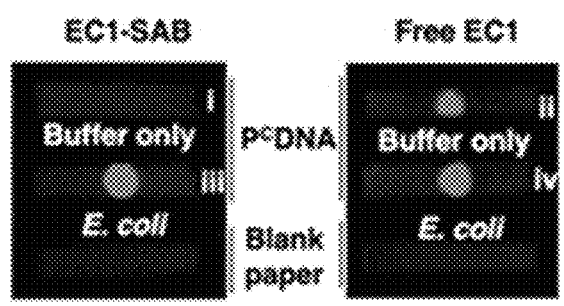
FIG. 1C
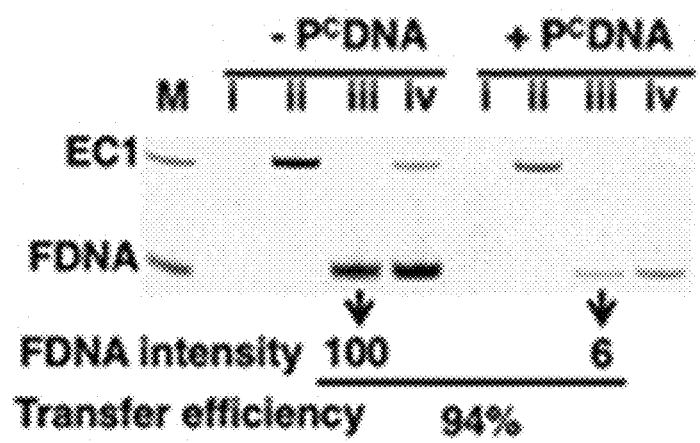

SEQUENCE LISTING

<160> NUMBER OF SEQ ID NOS: 13

<210> SEQ ID NO 1
<211> LENGTH: 109
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (25)..(25)
<223> OTHER INFORMATION: n is ribonucleic acid A

<400> SEQUENCE: 1
cgtgtgtcac aactcttcct agctntggtt cgatcaagag atgtgcgttg tcgagacctg    60
cgaccggaac actacactgt gtggggatgg atttctttac agttgtgtg              109

<210> SEQ ID NO 2
<211> LENGTH: 70
<212> TYPE: DNA
<213> ORGANISM: Artificial Sequence
<220> FEATURE:
<223> OTHER INFORMATION: Synthetic Construct

<400> SEQUENCE: 2
gatgtgcgtt gtcgagacct gcgaccggaa cactacactg tgtggggatg gatttcttta    60
cagttgtgtg                                                          70

<210> SEQ ID NO 3
<211> LENGTH: 39
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (25)..(25)
<223> OTHER INFORMATION: n is ribonucleic acid A

<400> SEQUENCE: 3
cgtgtgtcac aactcttcct agctntggtt cgatcaaga                           39

<210> SEQ ID NO 4
<211> LENGTH: 109
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (25)..(25)
<223> OTHER INFORMATION: n is ribonucleic acid A

<400> SEQUENCE: 4
cgtgtgtcac aactcttcct agctntggtt cgatcaagag atgtgcgttg tcgagacctg    60
cgaccggaac actacactgt gtggggatgg atttctttac agttgtgtg              109

<210> SEQ ID NO 5
<211> LENGTH: 44
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (30)..(30)
<223> OTHER INFORMATION: n is ribonucleic acid A

<400> SEQUENCE: 5
tttttcgtgt gtcacaactc ttcctagctn tggttcgatc aaga                     44

<210> SEQ ID NO 6
<211> LENGTH: 26
<212> TYPE: DNA
<213> ORGANISM: Artificial Sequence
<220> FEATURE:

<223> OTHER INFORMATION: Synthetic Construct

<400> SEQUENCE: 6
caagacgcac atctcttgat cgaacc        26

<210> SEQ ID NO 7
<211> LENGTH: 25
<212> TYPE: DNA
<213> ORGANISM: Artificial Sequence
<220> FEATURE:
<223> OTHER INFORMATION: Synthetic Construct

<400> SEQUENCE: 7
cgtgtgtcac aactcttcct agcta        25

<210> SEQ ID NO 8
<211> LENGTH: 122
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (25)..(25)
<223> OTHER INFORMATION: n is dabcyl-dT
<220> FEATURE:
<221> NAME/KEY: misc_feature
<222> LOCATION: (26)..(26)
<223> OTHER INFORMATION: n is ribonucleic acid A
<220> FEATURE:
<221> NAME/KEY: misc_feature
<222> LOCATION: (27)..(27)
<223> OTHER INFORMATION: n is fluorescein-dT

<400> SEQUENCE: 8 ttttttttt ttctatgaac tgacnnngac ctcactacca agatgccatc ctaccaacca        60
tgactggttt gtactaagag atttcaggca tcgctgcacg tcgtaggtga gctctgaact      120
cg      122

<210> SEQ ID NO 9
<211> LENGTH: 80
<212> TYPE: DNA
<213> ORGANISM: Artificial Sequence
<220> FEATURE:
<223> OTHER INFORMATION: Synthetic Construct

<400> SEQUENCE: 9
atgccatcct accaaccatg actggtttgt actaagagat ttcaggcatc gctgcacgtc        60
gtaggtgagc tctgaactcg       80

<210> SEQ ID NO 10
<211> LENGTH: 42
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (25)..(25)
<223> OTHER INFORMATION: n is dabcyl-dT
<220> FEATURE:
<221> NAME/KEY: misc_feature
<222> LOCATION: (26)..(26)
<223> OTHER INFORMATION: n is ribonucleic acid A
<220> FEATURE:
<221> NAME/KEY: misc_feature
<222> LOCATION: (27)..(27)
<223> OTHER INFORMATION: n is fluorescein-dT

```
<400> SEQUENCE: 10
tttttttttt ttctatgaac tgacnnngac ctcactacca ag                              42

<210> SEQ ID NO 11
<211> LENGTH: 31
<212> TYPE: DNA
<213> ORGANISM: Artificial Sequence
<220> FEATURE:
<223> OTHER INFORMATION: Synthetic Construct

<400> SEQUENCE: 11
gttggtagga tggcatcttg gtagtgaggt c                                          31

<210> SEQ ID NO 12
<211> LENGTH: 31
<212> TYPE: DNA
<213> ORGANISM: Artificial Sequence
<220> FEATURE:
<223> OTHER INFORMATION: Synthetic Construct

<400> SEQUENCE: 12
tttttttagc taggaagagt tgtgacacac g                                          31

<210> SEQ ID NO 13
<211> LENGTH: 28
<212> TYPE: DNA
<213> ORGANISM: Artificial Sequence
<220> FEATURE:
<223> OTHER INFORMATION: Synthetic Construct

<400> SEQUENCE: 13
ttttgtcagt tcatagaaaa aaaaaaaa                                              28
```

NUCLEIC ACID CLEAVING ENZYME-BASED BIOSENSOR AND METHODS OF USE THEREOF

RELATED APPLICATION

This disclosure claims benefit of U.S. Provisional Patent Application Ser. No. 62/979,703 filed Feb. 21, 2020, incorporated herein by reference in its entirety.

INCORPORATION OF SEQUENCE LISTING

A computer readable form of the Sequence Listing "P61048US01 Sequence Listing_ST25" (4,029 bytes), submitted via EFS-WEB and created on Feb. 17, 2021, is herein incorporated by reference.

FIELD

The present disclosure relates to biosensors that detect analytes, and in particular, biosensors based on nucleic acid cleaving enzymes such as RNA-cleaving DNAzymes and methods of use thereof.

BACKGROUND

There is a constant drive for the development of ultrasensitive biosensing methods that can afford great operational simplicity, together with cost effectiveness, for the purpose of detecting very low concentrations of biomarkers usually associated with human diseases or trace levels of harmful agents in food, water, and the environment [1].

Traditional biosensing methods based simply on the binding interactions between a molecular recognition element (MRE) and its cognate target are rarely able to achieve the high sensitivity required to be of use for detection. One solution to this problem is to combine target—MRE recognition with a signal-amplification mechanism. It has been shown, for example, that DNA aptamers and DNAzymes as MREs can be combined with DNA amplification strategies, such as rolling circle amplification (RCA), to achieve the ultrasensitive detection of a wide range of targets [2]. DNAzymes are single-stranded DNA molecules with catalytic activity [3] and can be derived from random-sequence DNA pools by using the technique of in vitro selection [4]. RNA-cleaving DNAzymes represent one of the best-studied classes of DNAzymes and have been widely used for analytical and bioanalytical applications [5], as is highlighted by many reported biosensors for metal ions or for small-molecule metabolites, as well as for bacterial and mammalian targets [6]. Although incorporation of enzymatic amplification such as RCA can significantly enhance detection sensitivity, additional steps are required, and expensive and delicate DNA polymerases are used, thus increasing the cost and complexity of the assay. Therefore, there is a significant need for sensitive nucleic acid-cleaving DNAzyme biosensing methods that do not rely on enzymatic amplification such as RCA.

SUMMARY

The present disclosure describes an approach for creating a simple sensor for the detection of an analyte that does not require enzymatic amplification. The biosensor comprises the use of a nucleic acid cleaving enzyme such as a ribonucleotide-cleaving DNAzyme (RNA-cleaving DNAzyme) and a strategy designed to capture the cleavage product in a defined area (microzone), thereby enriching the concentration of the cleavage product, using a first support loaded with a nucleic acid substrate and a second support containing a microzone covered with nucleic acid binding molecules such as DNA oligonucleotides capable of capturing a cleavage product through interaction such as Watson-Crick hybridization, whereby the cleavage product was produced by the nucleic acid cleaving enzyme cleaving the nucleic acid substrate.

Accordingly, the present disclosure provides a biosensor for the detection of an analyte comprising:

a) i) a nucleic acid substrate coupled to a first support and a nucleic acid cleaving enzyme; or
  ii) a nucleic acid cleaving enzyme comprising a nucleic acid substrate coupled to a first support; and
b) a nucleic acid binding molecule coupled to a microzone on a second support;
wherein the nucleic acid substrate comprises a detection moiety;
wherein the nucleic acid enzyme is capable of cleaving the nucleic acid substrate;
wherein the nucleic acid cleaving enzyme is activated upon contact with the analyte, thereby cleaving the nucleic acid substrate to release a cleavage product comprising the detection moiety; and
wherein the nucleic acid binding molecule binds to the cleavage product.

In some embodiments, the nucleic acid cleaving enzyme is an RNA-cleaving DNAzyme, a DNA-cleaving DNAzyme, a ribozyme, or an endonuclease that has DNA and/or RNA cleaving activities.

In some embodiments, the nucleic acid cleaving enzyme is an RNA-cleaving DNAzyme and the nucleic acid binding molecule is an oligonucleotide.

In some embodiments, the microzone is about 0.5 mm to 5 mm in diameter.

In some embodiments, the first support comprises, but not limited to, modified agarose beads, graphene oxide, gold nanoparticles or glass beads. In some embodiments, the first support comprises modified agarose beads, graphene oxide, gold nanoparticles or glass beads, and wherein the nucleic acid substrate is coupled to the first support by covalent or non-covalent immobilization chemistry. In some embodiments, a surface of the first support is modified with immobilization chemistries comprising, but not limited to, streptavidin, covalent strategies such as cyanuric chloride, isothiocyanate, nitrophenyl chloroformate, hydrazine, amino, thiol, acrydite, NHS ester activated, aldehyde, azlactone-activated, carbonyl diimidazole activated, maleimide, iodoacetyl-activated, and biotin chemistries, and non-covalent strategies such as adsorption. In some embodiments, the second support comprises, but not limited to paper, a paper-based product such as nitrocellulose, glass fiber substrate, graphene paper, modified agarose beads, graphene oxide, gold nanoparticles or glass beads. In some embodiments, the paper or paper-based product is nitrocellulose.

In some embodiments, the microzone is created by hydrophobic material printing. In some embodiments, the microzone is created by partitioning of two surface types, comprised but not limited to wax printing, and covered with the nucleic acid binding molecule such as activated or functionalized DNA oligonucleotides bound to a reactive group (e.g. avidin, streptavidin, neutravidin, captavidin) that are conjugated within the microzone of the second support. In some embodiments, the nucleic acid binding molecule is conjugated to biotin and the second support is conjugated to streptavidin, and wherein the biotin is bound to the streptavidin.

In a further embodiment, the biosensor comprising the first support and the second support is placed in a target-containing test solution allowing the nucleic acid cleaving enzyme, such as an RNA-cleaving DNAzyme molecule, to undergo target-induced cleavage, such as RNA-cleavage, thereby releasing a cleavage product such as a DNA fragment. The cleavage product is captured on the second support by binding interaction, such as complementary hybridization, to a nucleic acid binding molecule, such as an immobilized DNA probe. This strategy is very effective in achieving high levels of detection sensitivity, being able to enrich the concentration of the cleavage product by several orders of magnitude.

In some embodiments, the detection moiety is detected by a detection system. In some embodiments, the detection system comprises a fluorescent, colorimetric, chemiluminescent, radiolabeled, or electrochemical detection system. In some embodiments, the fluorescent detection system comprises a fluorescent moiety. In some embodiments, the fluorescent moiety comprises, but not limited to fluorescein amidites (FAM), other fluorescein dyes, cyanine dyes, rhodamine dyes, TYE™ dyes, ATTO™ dyes, Alexa Fluor® dyes, LI-COR IRDyes®, and any other fluorescent dye that can be incorporated into the biosensor. In some embodiments, the colorimetric detection system comprises an enzymatic moiety comprising, but not limited to urease, alkaline phosphatase, horseradish peroxidase, glucose oxidase, and β-galactosidase. In some embodiments, the biosensor comprises a chemiluminescent, radiolabeled, or electrochemical detection system. This disclosure provides a platform for developing ultrasensitive biosensors that take advantage of the widely available nucleic acid cleaving enzymes, such as RNA-cleaving DNAzymes, as molecular recognition elements.

In some embodiments, the biosensor further comprises i) one or more additional nucleic acid substrates coupled to the first support, and one or more additional nucleic acid enzymes, or ii) one or more additional nucleic acid cleaving enzymes each comprising one of one or more additional nucleic acid substrates coupled to the first support, wherein each of the one or more nucleic acid substrates comprises a detection moiety, wherein each of the one or more additional nucleic acid cleaving enzymes is activated upon contact with one of one or more additional analytes, thereby cleaving the one or more additional nucleic acid substrates to release one or more additional cleavage products each comprising a detection moiety;
  wherein each of the one or more additional nucleic acid cleaving enzymes is specific to one of the one or more additional analytes; and each of the one or more additional nucleic acid cleaving enzyme is specific to one of the one or more additional acid substrates;
  wherein the biosensor further comprises one or more additional nucleic acid binding molecules, each of the one or more additional nucleic acid binding molecules binds to one of the one or more additional cleavage products; and
  wherein each of the one or more additional nucleic acid binding molecules is concentrated within one of one or more additional microzones on the second support.

Also provided is a method for the detection of at least one analyte in a sample, the method comprising:
  a) placing the biosensor of the present disclosure into a test solution comprising the sample;
  b) retrieving the second support from the test solution; and
  c) detecting the presence of the at least one analyte on the second support.

In some embodiments, the method further comprises after step b), washing the second support. In some embodiments, the method comprises a biosensor having i) one or more additional nucleic acid substrates coupled to the first support and one or more additional nucleic acid cleaving enzymes, or ii) one or more additional nucleic acid enzymes each comprising one of one or more additional nucleic acid substrates coupled to the first support, and one or more additional nucleic acid binding molecules. In some embodiments, the test solution is up to about 100 mL.

Also provided is a kit for detecting an analyte, wherein the kit comprises the biosensor of the present disclosure, and instructions for use of the kit for detecting an analyte. In some embodiments, the biosensor comprises i) one or more additional nucleic acid substrates coupled to the first support and one or more additional nucleic acid cleaving enzymes, or ii) one or more additional nucleic acid cleaving enzymes each comprising one of one or more additional nucleic acid substrates coupled to the first support, wherein each of the one or more additional nucleic acid cleaving enzymes is capable of being activated by one of one or more additional analytes, and one or more additional nucleic acid binding molecules.

In some embodiments, the kit further comprises one or more of a) container, b) buffer, c) washing solution, and d) wherein the detection system comprises i) substrate for an enzymatic moiety, ii) substrate for chemiluminescent detection, and/or iii) color changing dye.

Other features and advantages of the present disclosure will become apparent from the following detailed description. It should be understood, however, that the detailed description and the specific examples, while indicating embodiments of the disclosure, are given by way of illustration only and the scope of the claims should not be limited by these embodiments, but should be given the broadest interpretation consistent with the description as a whole.

DRAWINGS

The embodiments of the disclosure will now be described in greater detail with reference to the attached drawings in which:

FIG. 1A shows the conceptual framework of surface-to-surface product enrichment (S2SPE) sensing method in exemplary embodiments of the disclosure.

FIG. 1B shows results of FDNA1 captured by $P^C$DNA in exemplary embodiments of the disclosure. The paper strip was incubated with i) EC1-SAB and reaction buffer only, ii) free EC1 and reaction buffer only, iii) EC1-SAB in the presence of E. coli, and iv) free EC1 in the presence of E. coli.

FIG. 1C shows 10% dPAGE analysis of DNA sequences from the reaction mixtures in FIG. 1B in exemplary embodiments of the disclosure. M represents the mixture of uncleaved EC1 and FDNA generated by treatment of EC1 with 0.2 M NaOH at 90° C. for 5 min. $10^6$ CFU mL$^{-1}$ of E. coli cells were used in the experiments.

Figure 2A:
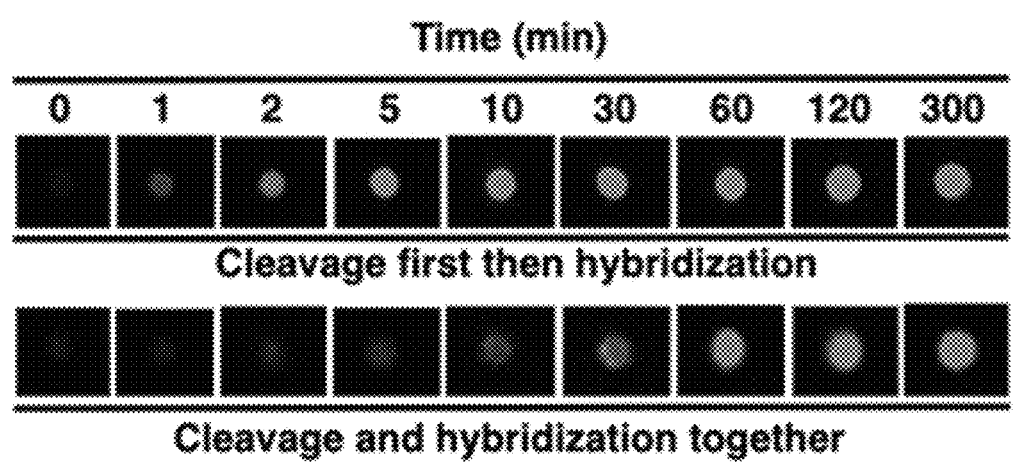

FIG. 2A shows the time-dependent fluorescence intensities observed with the paper with capture DNA ($P^C$DNA) for two scenarios (cleavage first then hybridization, or cleavage and hybridization together) in exemplary embodiments of the disclosure. Fluorescence of $P^C$DNA hybridized with FDNA in two scenarios: 1) EC1 cleavage reaction with the activating target for 2 h, followed by hybridization (top images), and 2) cleavage and hybridization reactions conducted in a single step.

Figure 2B:
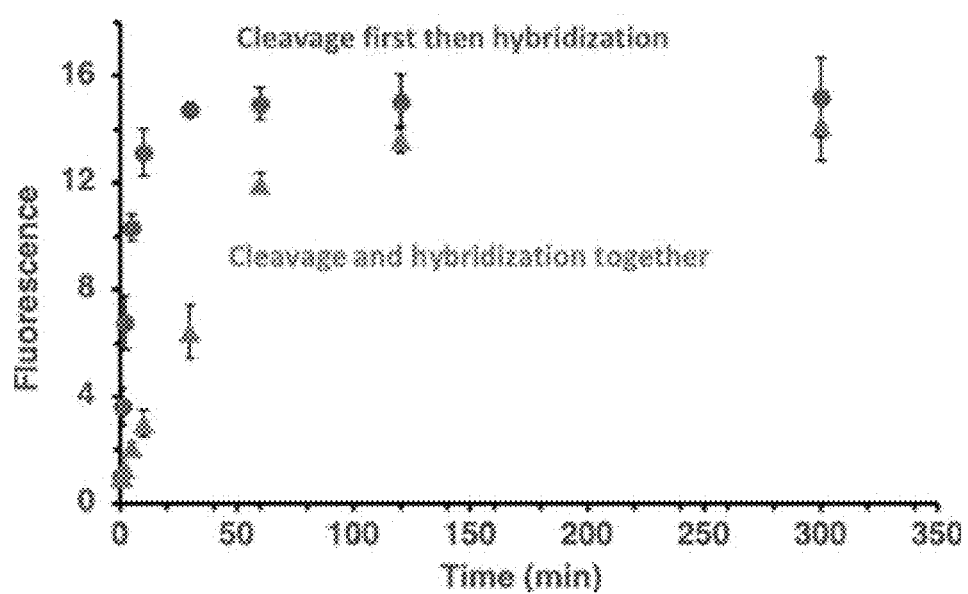

FIG. 2B shows fluorescence quantification of the two reactions in FIG. 2B in exemplary embodiments of the disclosure. $10^7$ CFU mL$^{-1}$ of $E.$ $coli$ cells were used in this experiment. Circles are data points from cleavage first then hybridization. Triangles are data points from cleavage and hybridization together.

Figure 3A:
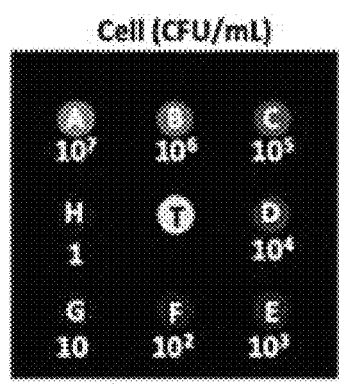

FIG. 3A shows the design of a P$^C$DNA plate printed with multiple reference zones and with a test zone (T) in the middle in exemplary embodiments of the disclosure.

Figure 3B:
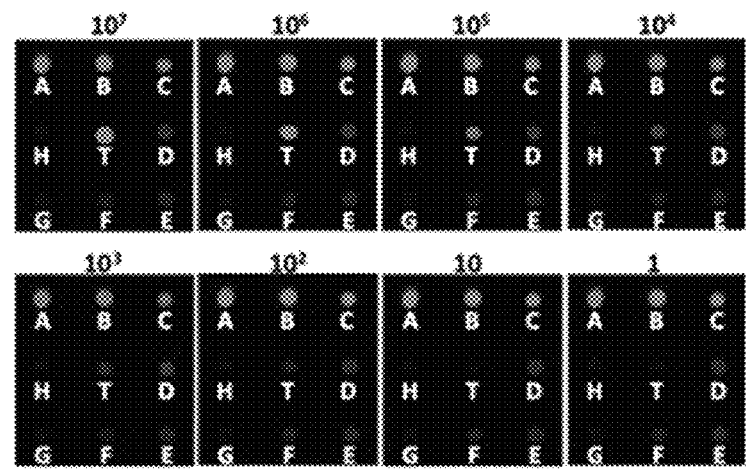

FIG. 3B shows signal production in response to different concentrations of $E.$ $coli$ cells in exemplary embodiments of the disclosure.

Figure 3C:
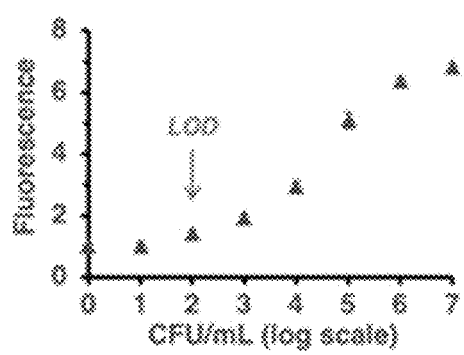

FIG. 3C shows fluorescence signals of the test zones versus the concentration of $E.$ $coli$. The limit of detection (LOD) is indicated in exemplary embodiments of the disclosure.

Figure 3D:
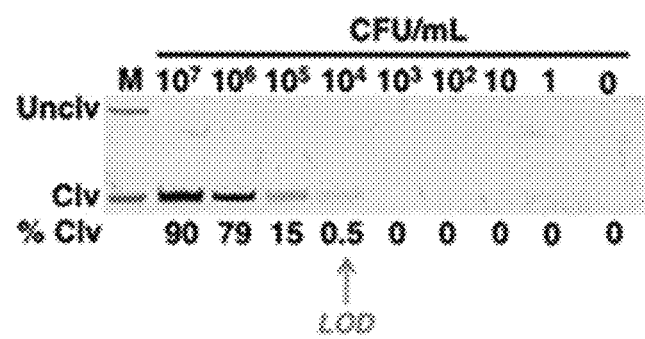

FIG. 3D shows 10% dPAGE analysis of cleavage in the presence of different concentrations of $E.$ $coli$. The limit of detection (LOD) is indicated in exemplary embodiments of the disclosure.

Figure 4A:
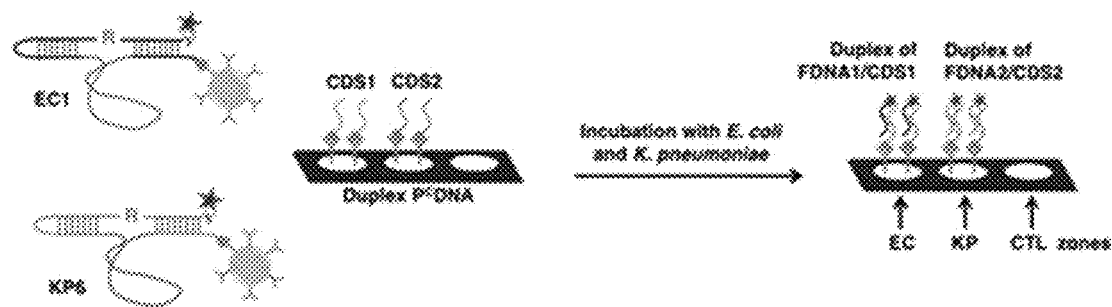

FIG. 4A shows the design of a duplex assay with EC1 and KP6, RNA-cleaving DNAzymes activated by $E.$ $coli$ and $K.$ $pneumoniae$, respectively, in exemplary embodiments of the disclosure. This provides a demonstration of the multiplex detection capability in exemplary embodiments of the disclosure. Each DNAzyme, upon cleavage, produces a fluorescent cleavage product that can be captured by the duplex P$^C$DNA containing three zones: EC zone, KP zone, and control zone (CTL). The EC zone and the KP zone are each treated with a capture DNA sequence that binds to FDNA1 and FDNA2, respectively. The control zone does not contain any capture DNA.

Figure 4B:
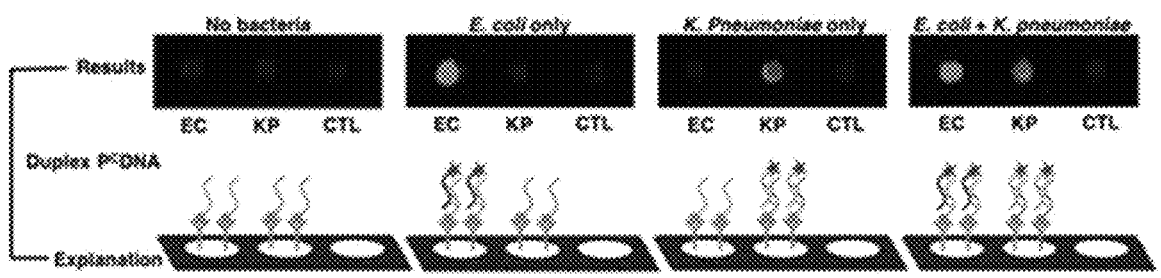

FIG. 4B shows representative fluorescence images of the duplex P$^C$DNA sensors retrieved from the reaction mixtures of EC1/KP6-SAB treated with no bacteria, $E.$ $coli$ only, $K.$ $pneumoniae$ only, and both $E.$ $coli$ and $K.$ $pneumoniae$, in exemplary embodiments of the disclosure. $10^6$ CFU mL$^{-1}$ of $E.$ $coli$ and $K.$ $pneumoniae$ cells were used in the experiment.

Figure 5A:
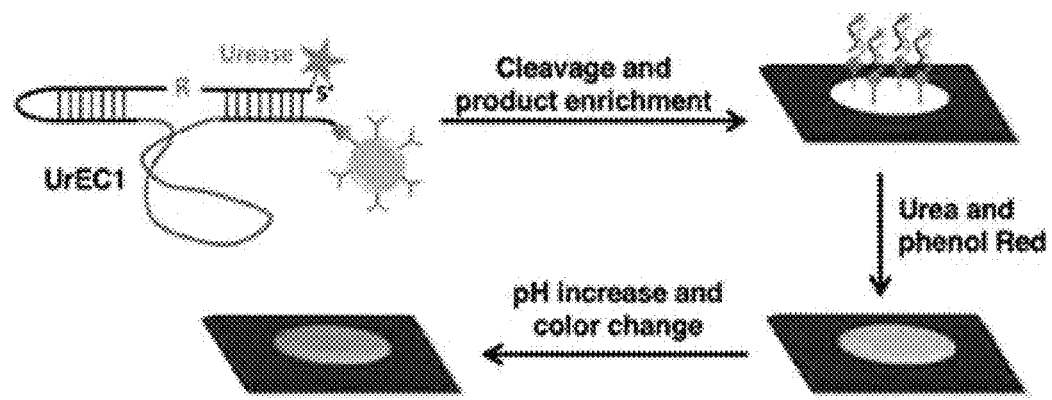

FIG. 5A shows a schematic illustration of the test principle of the colorimetric assay based on urease-labeled EC1 in an exemplary embodiment of the disclosure.

Figure 5B:
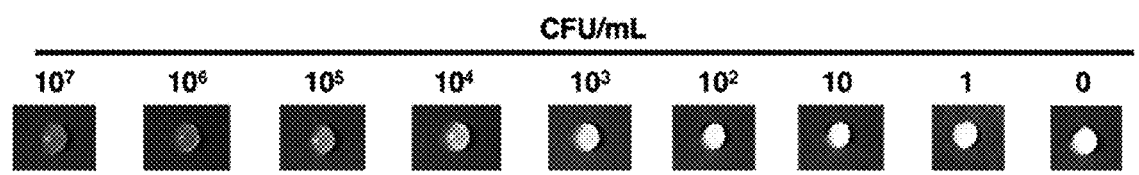

FIG. 5B shows results of colorimetric S2SPE assay in exemplary embodiments of the disclosure. Color development of P$^C$DNA was detected after treatment with different concentrations of $E.$ $coli$. The photographs were taken after a signal-producing time of 10 min.

Figure 5C:
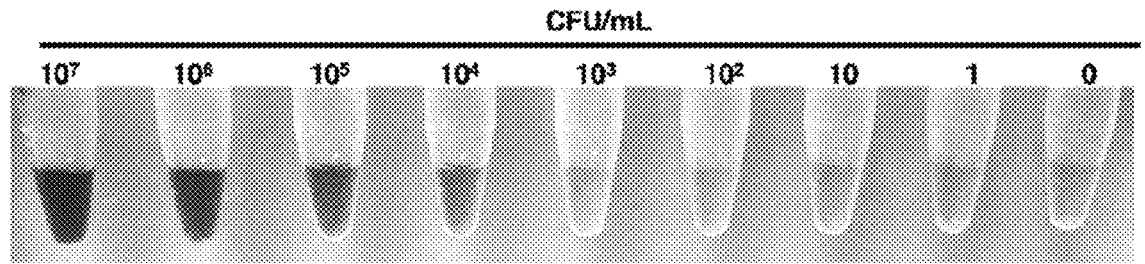

FIG. 5C shows results of solution-based litmus test in exemplary embodiments of the disclosure. The photograph was taken after a signal-producing time of 60 min.

Figure 6A:
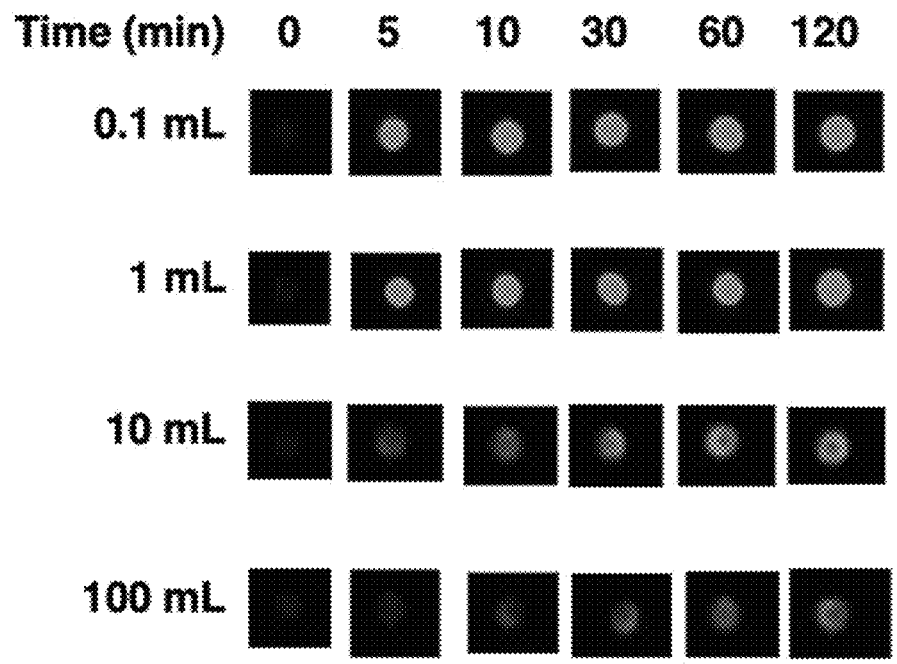

FIG. 6A shows representative fluorescent images of the effect of the sample volume on the hybridization rate of 5 pmol FDNA1 to P$^C$DNA in varying sample volumes indicated in exemplary embodiments of the disclosure. In these experiments, the EC1 cleavage reaction and the FDNA1/P$^C$DNA hybridization reaction were performed separately. Specifically, for all sample volumes, 5 pmol of the bead-bound EC1 was incubated with the test sample for two hours to induce full cleavage of EC1. Following 2 h cleavage reaction, P$^C$DNA, which was prepared in the same manner for all sample volumes as described in "preparation of P$^C$DNA (paper sensor with capture DNA)" above, was placed inside each reaction mixture. The paper from each sample was taken out at certain time points, washed and scanned with a Chemidoc™ fluorescence imager.

Figure 6B:
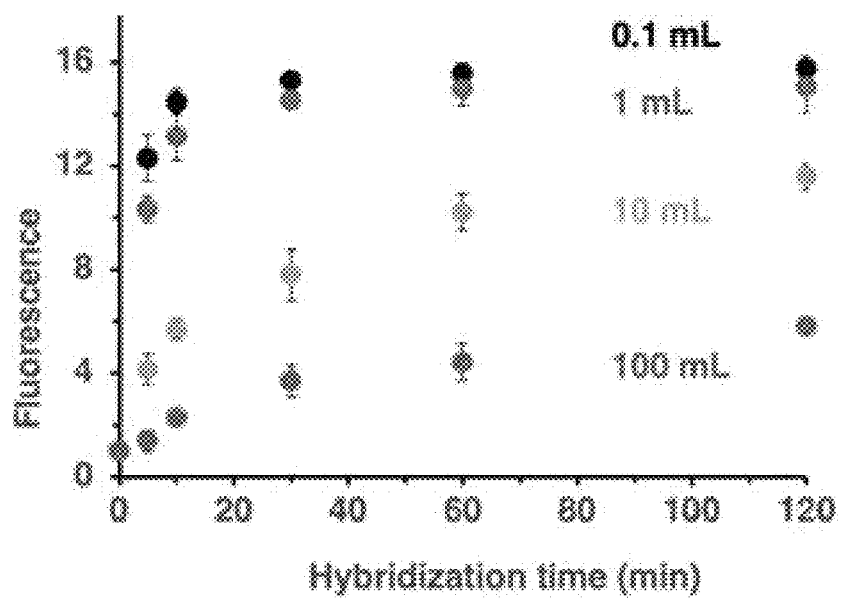

FIG. 6B shows quantified fluorescence signal from FIG. 6A in exemplary embodiments of the disclosure. $10^7$ CFU/mL of $E.$ $coli$ cells were used in the experiments.

Figure 7:
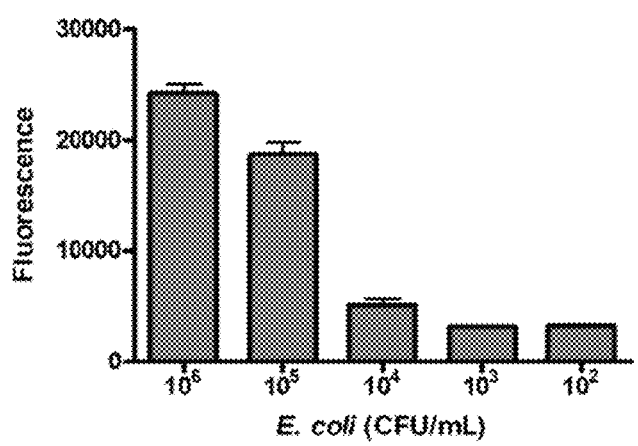

FIG. 7 shows the detection sensitivity of EC1-SAB mediated RCA based assay in an exemplary embodiment of the disclosure. 500 μL of 2×RB and a relevant CIM of $E.$ $coli$, based on the number of cells needed for each experiment were added to EC1-SAB (containing 5 pmol of EC1). The final volume of the mixture was adjusted to 1 mL by adding ddH2O. After incubation at room temperature for 120 minutes, 30 μL of the supernatant containing the cleavage fragment of EC1 was mixed with 1 μL of PNK (10 U μL$^{-1}$) and incubated at 37° C. for 30 min. The RCA reaction was then initiated by the addition of 1 μL (1 μM) of circular DNA template, 1 μL of Φ29DNA polymerase (10 U μL$^{-1}$), 5 μL of dNTPs (10 mM), 5 μL of 10×RCA reaction buffer, 5 μL of 10×SYBR Gold and 4 μL of water. These reactions were carried out in a microplate scanning spectrometer (TECAN M1000) set to a constant temperature of 30° C. Fluorescence intensities were collected after 120 min of incubation.

Figure 8:
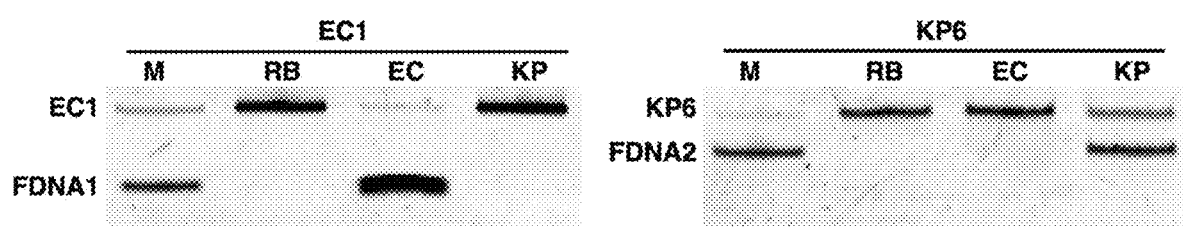

FIG. 8 shows a 10% dPAGE analysis of the activity of EC1 and KP6 toward reaction buffer alone (RB), $E.$ $coli$ (EC) and $K.$ $pneumoniae$ (KP) in exemplary embodiments of the disclosure. $10^6$ CFU/mL of bacterial cells were used in this experiment. The marker (M) is a sample of EC1 or KP6 that has been heat treated with NaOH (at 90° C. for 5 min), which creates mixture of the cleavage product (FDNA1 or FDNA2) and the uncleaved DNAzyme (EC1 or KP6).

Figure 9A:
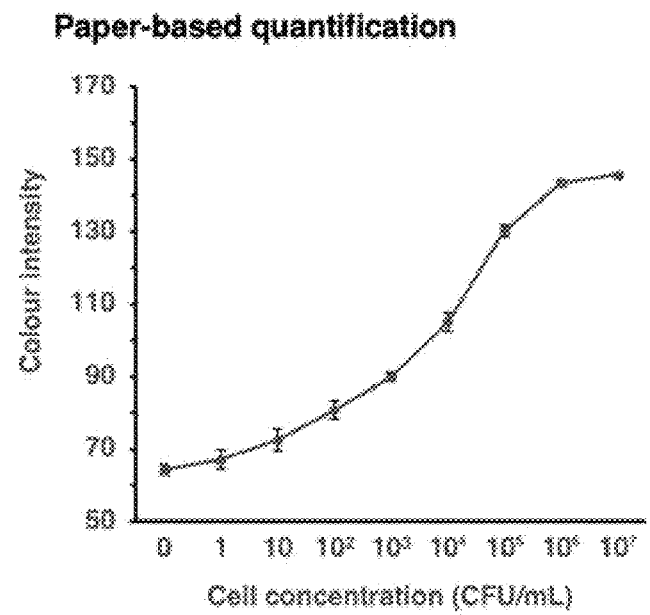

FIG. 9A shows quantification of the P$^C$DNA-based colorimetric assay represented in FIG. 5B in exemplary embodiments of the disclosure.

Figure 9B:
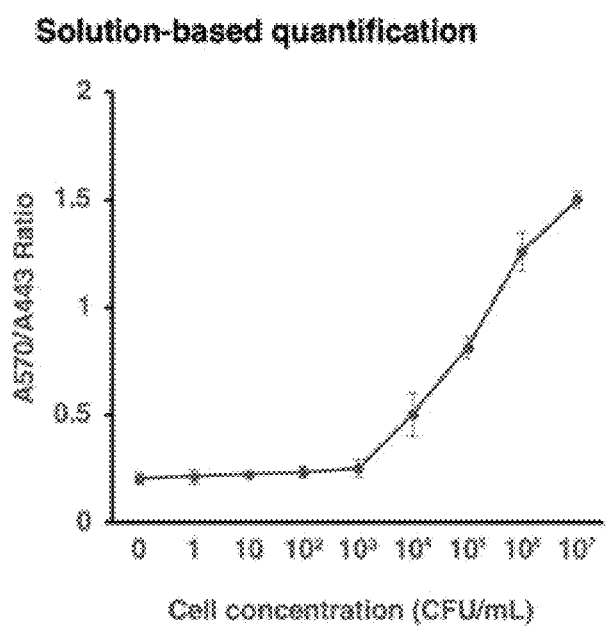

FIG. 9B shows quantification of the solution-based colorimetric assay represented in FIG. 5C in exemplary embodiments of the disclosure.

Figure 10A:
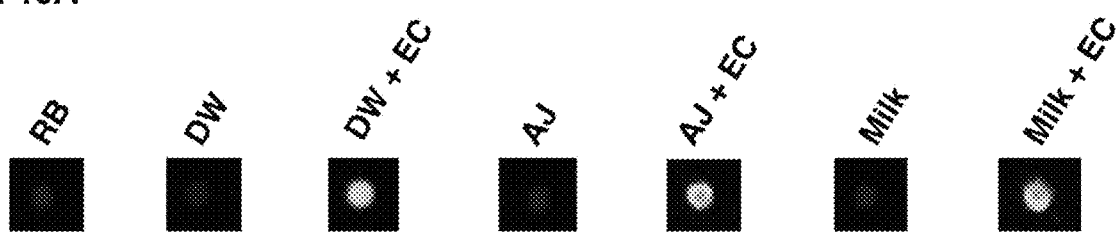

FIG. 10A shows results of fluorescent assay where the papers were imaged using a Chemidoc™ fluorescence imager in exemplary embodiments of the disclosure. The results were from the use of the S2SPE assay in detecting $E.$ $coli$ (EC) in drinking water (DW), apple juice (AJ), and milk samples, in exemplary embodiments of the disclosure. RB is the sample with reaction buffer alone. $10^5$ CFU/mL of $E.$ $coli$ cells were used in these experiments.

Figure 10B:
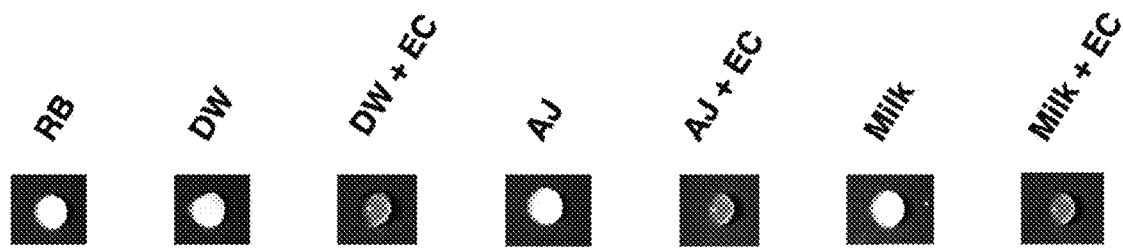

FIG. 10B shows result of colorimetric assay where the papers were photographed after 10 min of color development in exemplary embodiments of the disclosure. RB: reaction buffer; EC; $E.$ $coli$, DW: drinking water; AJ: apple juice.

DETAILED DESCRIPTION

I. Definitions

Unless otherwise indicated, the definitions and embodiments described in this and other sections are intended to be applicable to all embodiments and aspects of the present disclosure herein described for which they are suitable as would be understood by a person skilled in the art.

The term "biosensor" as used herein refers to an analytical device used for the detection of an analyte, which comprises a biological component such as nucleic acids or proteins. A biosensor can be part of a larger biosensor system or is itself a biosensor system.

The term "analyte" as used herein may refer to any agent, including but not limited to, metal ions, small molecules, whether organic or inorganic, drugs, hormonal growth factors, biomolecules, toxins, biopolymer such as nucleic acids, carbohydrates, lipids, peptides, proteins, and viruses, microorganisms such as bacteria, and cells, for which one would like to sense or detect. The analyte may be either isolated from a natural source or synthetic. The analyte may be a single compound or a class of compounds, such as a class of compounds that share structural or functional features.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The recitation of numerical ranges by endpoints herein includes all numbers and fractions subsumed within that range (e.g. 1 to 5 includes for example 1, 1.5, 2, 2.75, 3, 3.90, 4, and 5). It is also to be understood that all numbers and fractions thereof are presumed to be modified by the term "about".

As used in this disclosure, the singular forms "a", "an" and "the" include plural references unless the content clearly dictates otherwise.

In embodiments comprising an "additional" or "second" component, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "sample" or "test sample" as used herein refers to any material in which the presence or amount of an analyte is unknown and can be determined in an assay. The sample may be from any source, for example, any biological (e.g. human or animal samples, including clinical samples), environmental (e.g. water, soil or air) or natural (e.g. plants) source, or from any manufactured or synthetic source (e.g. food or drinks). The sample may be comprised or is suspected of comprising one or more analytes. The sample may be a "biological sample" comprising cellular and non-cellular material, including, but not limited to, tissue samples, saliva, sputum, urine, blood, serum, other bodily fluids and/or secretions. In some embodiments, the sample comprises saliva, sputum, oropharyngeal and/or nasopharyngeal secretions. In some embodiments, the sample comprises a food or a drink. In some embodiments, the drink comprises drinking water, juice such as apple juice or orange juice, or dairy drink such as milk or yogurt drink.

The term "test solution" as used herein refers to a solution that contains the sample. The test solution can be any aqueous solution compatible for the use of the presently disclosed biosensor and methods for using same. The test solution may be entirely comprised of the sample or it may be a dilution of the sample.

The term "nucleic acid" as used herein refers to biopolymer comprising monomers of nucleotides, such as deoxyribonucleic acid (DNA), ribonucleic acid (RNA) and other polynucleotides of modified nucleotides and/or nucleotide derivatives, and may be either double stranded (ds) or single stranded (ss). In some embodiments, modified nucleotides may contain one or more modified bases (e.g. unusual bases such as inosine, and functional modifications to the bases such as amino), modified backbones (e.g. peptide nucleic acid, PNA) and/or other chemically, enzymatically, or metabolically modified forms.

The term "nucleic acid cleaving enzyme" as used herein refers to any molecule that accelerates or catalyzes the cleavage of a nucleic acid. The term enzyme as used herein refers to all types of enzymes including protein enzymes, DNAzymes and ribozymes, including allosteric versions which activity is regulated by binding of an effector molecule at a site other than the enzyme's active site. The nucleic acid cleaving enzyme can comprise a nucleic acid substrate, whether through covalent or non-covalent interactions, such as hybridization.

The term "DNAzyme" as used herein refers to a nucleic acid molecule or oligonucleotide sequence that can catalyze or initiate a reaction. DNAzymes may be single-stranded DNA, and may include RNA, modified nucleotides and/or nucleotide derivatives. In some embodiments, the substrate is a nucleic acid. In some embodiments, the DNAzyme is a trans-acting DNAzyme. In some embodiments, the DNAzyme is a cis-acting DNAzyme. In some embodiments, the DNAzyme self-cleaves. In some embodiments, the substrate of the DNAzyme is a DNAzyme that includes RNA. In some embodiments, the DNAzyme cleaves a single ribonucleotide linkage. In some embodiments, the trans-acting DNAzyme cleaves a single ribonucleotide linkage. In some embodiments, the cis-acting DNAzyme cleaves a single ribonucleotide linkage. In some embodiments, the single ribonucleotide linkage is in a nucleic acid sequence wherein the remaining nucleotides are ribonucleotides. In some embodiments, the single ribonucleotide linkage is in a nucleic acid sequence wherein the remaining nucleotides are deoxyribonucleotides. In some embodiments, the DNAzyme is RNA-cleaving and catalyzes the cleavage of a particular substrate, for example a nucleic acid sequence comprising one or more ribonucleotides, at a defined cleavage site. In some embodiments, the DNAzyme cleaves a nucleic acid sequence at a single ribonucleotide linkage thereby producing a nucleic acid cleavage fragment or a cleavage product.

Methods for generating RNA-cleaving DNAzyme specific to an analyte is known to the person skilled in the art, for example, as described in Ali M M et al., Angew. Chem. Int. Ed. 2011, 50, 3751-3754, Aguirre D S et al., Biomolecules 2013, 3, 563-577, and U.S. Pat. No. 7,910,710B2, herein incorporated by reference in their entirety. For example, selection and isolation of RNA-cleaving autocatalytic DNAzyme specific to an analyte can be done on the basis of fluorescent signaling. A DNA construct which includes a ribonucleotide flanked by a fluorophore modified oligonucleotide and a quencher-modified oligonucleotide can be used. The construct also includes a site for insertion of random nucleotide sequences. If the inserted sequence has RNA cleaving activity, the ribonucleotide linkage is cleaved and the fluorophore is separated from the quencher and a fluorescent signal is generated. Several rounds of selection can be carried out to enrich for the catalytic sequence. The selection scheme involves generating a pool of single stranded DNA molecules that have a random sequence flanked by a predetermined 5' sequence and a predetermined 3' sequence. These DNA molecules are referred to as "library" DNA. An oligonucleotide, referred to as an "acceptor" oligonucleotide, has a fluorophore modified nucleotide, a quencher modified nucleotide and a ribonucleotide linkage positioned between the fluorophore and the quencher. Another oligonucleotide, termed "template" DNA, has a first sequence which is at least partially complementary to the sequence of the acceptor oligonucleotide and a second sequence which is at least partially complementary to the predetermined 5' sequence of the library DNA. Due to the complementarity of the sequences, the template DNA forms a duplex structure with the acceptor oligonucleotide and the library DNA and brings them into proximity. When a ligase is introduced, the library DNA is ligated to the acceptor oligonucleotide to form a ligated molecule. The duplex structure is dissociated and the ligated molecule can be separated from the template DNA by PAGE. The selection scheme is not limited to any particular sequence. The general scheme can be used to select a variety of DNA enzymes having different characteristics. The general scheme selects DNAzymes that are cis-acting, as covalent attachment of the substrate offers an easy way to select for an enzymatic activity, and these cis-acting DNAzymes can be readily made into trans-acting DNAzymes by separating the substrate sequence from the DNAzyme. Methods for selecting nucleic acid-cleaving DNAzymes are also known in the art, for example, as described in Carmi et al, Chemistry & Biology 1996, 3(12): 1039-1046, Wang, et al., Organic & Biomolecular Chemistry 2016, 14(7): 2347-2351, herein incorporated by reference in their entirety.

Enzymatic DNA molecules that require the presence of co-factors such as, but not limited to, small molecules, peptides, polypeptides, metal ions, metabolites, sugars, nucleic acids, bacteria, parts thereof, or extracellular mixture, whether crude or purified, virus or parts thereof, etc., are selected by incubating the ligated molecule in the presence of that factor. In this way, the factor would be the analyte detected by the eventual DNAzyme. If the ligated molecule comprises a DNA enzyme that is responsive to that factor, then cleavage occurs at the ribonucleotide linkage. This results in the generation of a fluorescent signal as the fluorophore and quencher become separated. The autocatalytic molecules can then be enriched through a series of polymerase chain reactions. Since the autocatalytic DNA will have the predetermined 3' sequence of the library DNA, a first primer complementary to that sequence can be used. A second primer has a sequence complementary to the acceptor oligonucleotide and the conserved 5' sequence of the pool DNA. PCR with these primers will generate DNA molecules having the sequence of the ligated DNA with the exception of the ribonucleotide. The ribonucleotide is then introduced using a third primer, which is ribo-terminated. After amplification, the DNA is treated with an RNA cleaving moiety, such as NaOH. The cleaved DNA is subjected to PAGE purification and DNA phosphorylation. The 5' phosphorylated DNA is used to initiate a further round of selection. Using this strategy highly selective RNA-cleaving DNAzyme can even be regenerated in situ. Adaptation of this method has been seen where crude extracellular mixture from a given microbe is directly used as the complex target (i.e. analyte), thus bypassing all target separation and identification steps (see, for instance, Ali M M et al., Angew. Chem. Int. Ed. 2011, 50, 3751-3754; herein incorporated by reference).

The term "ribozyme" as used herein refers to RNA molecules that are capable of catalyzing specific biochemical reactions. The activity of a ribozyme is similar to that of a protein enzyme, with a difference being the composition of the two. The ribozyme can be an allosteric ribozyme by which binding of an analyte is at a site other than the ribozyme's active site. A self-cleaving ribozyme is an RNA molecule that catalyzes cleavage and related reactions at a specific site within an RNA polymer. The term "aptazyme" as used herein refers to a ligand-activated self-cleaving ribozyme that contain integrated aptamer domains. In vitro selection methodology can be used to identify ribozymes, for example, as described in Robertson and Gerald, Nature 1990, 344(6265): 467-468, herein incorporated by reference.

As used herein, the term "coupled" and "tethered" are used interchangeably and refers to attachment by covalent bonds or by strong non-covalent interactions. Any method typically used by the person skilled in the art for the coupling of polymers such as nucleic acids to a support described herein can be used in the present disclosure.

As used herein the term "support" and "solid substrate" are used interchangeably and refers to a material, that is generally insoluble in aqueous solution including water or any commonly available laboratory buffer or solvent, on which polymers such as nucleic acids are synthesized, coupled or immobilized, or any solid or semi-solid material that is capable of being coupled to nucleic acids, such as a magnetic bead, glass and plastic. A support can be porous material that contains pores having substantially uniform diameters (for example in the nm range). Porous materials include paper or a paper-based product such as nitrocellulose, synthetic filters and the like. In such porous materials, a coupling reaction may take place within the pores. The nucleic acid and the support may be conjugated with molecules that have affinity for binding to each other. For example, where a nucleic acid is biotinylated and a support has streptavidin on it, the nucleic acid can be coupled to the support through the formation of the streptavidin-biotin complex. The support can have various shapes, such as pin, strip, plate, disk, rod, bends, cylindrical structure, particle, including bead, nanoparticle (e.g. gold nanoparticle) and the like. The support can have variable lengths and/or widths. For the first support described herein, large beads can be useful when used in combination with a second support that is paper-based for at least two reasons: 1) because of their large size the beads are not entrapped within the paper pores (2-4 μm in diameter, much smaller than the bead size of 35 μm in diameter), and 2) larger beads are associated with bigger drag force that pushes the beads away from the surface when the paper sensor with captured cleavage product is washed. In some embodiments, the first support comprises large beads. In some embodiments, the first support comprises large beads having bead size of about 25 μm to 50 μm in diameter. In some embodiments, the bead size is about 30 μm to 40 μm in diameter. In some embodiments, the bead size is about 35 μm in diameter.

The term "microzone" as used herein refers to a defined region on a support which is coupled to nucleic acid binding molecule. For creating the microzone, a hydrophobic material such as wax or any other hydrophobic material that is generally impermeable to aqueous solutions can be printed onto a support to partition the surface for creating the microzone. The microzone can have a diameter that is suitable for concentrating cleavage products for enriching detection signal. For example, the microzone can be about 0.5 mm to 5 mm in diameter, about 1 mm to 4 mm in diameter, about 1.5 mm to 3 mm in diameter, or about 2 mm in diameter.

The term "nucleic acid substrate" as used herein refers to a substrate of a nucleic acid cleaving enzyme. The nucleic acid cleaving enzyme can process a nucleic acid substrate to produce two parts, including the cleavage product. The nucleic acid substrate can be a part of the nucleic acid cleaving enzyme itself, such as being coupled or hybridized to the nucleic acid cleaving enzyme, or as a separate molecule, so long as it is cleavable by the nucleic acid cleaving enzyme. Where the nucleic acid cleaving enzyme is cis-acting, it can cleave the nucleic acid substrate that is part of it or coupled or hybridized to it. When the nucleic acid cleaving enzyme is trans-acting, it can cleave a nucleic acid substrate that is a separate molecule. For example, if the nucleic acid substrate is coupled to a support, a trans-acting nucleic acid cleaving enzyme can be coupled to the support or it can be free in a solution, for it to cleave the nucleic acid substrate. A nucleic acid cleaving enzyme can also be both cis-acting and trans-acting. In some embodiment, the nucleic acid substrate comprises a detection moiety.

The term "hybridizes", "hybridized" or "hybridization" as used herein refers to the sequence specific non-covalent binding interaction with a complementary, or partially complementary, nucleic acid sequence.

The term "detection system" as used herein refers to any means that produces a signal that is detectable, for example, using fluorescent, colorimetric, chemiluminescent, radiolabeled, or electrochemical methods. The detection system includes use of detection moiety (also referred to as signal transducer) such as fluorescent moiety (or fluorescent detection moiety), colorimetric detection moiety that uses for example, an enzymatic moiety, chemiluminescent moiety (or chemiluminescent detection moiety), electrochemical moiety (or electrochemical detection moiety), or radiolabeled moiety (or radiolabeled detection moiety). For example, the moiety may be a label coupled to the region of the nucleic acid substrate that is to be released upon contact with an analyte.

II. Biosensors, Methods of Use, and Kits

The present disclosure describes nucleic acid-cleaving enzyme-based biosensor and methods of use thereof. It is a biosensor for detecting an analyte which does not require enzymatic amplification such as rolling circle amplification (RCA), thereby reducing the cost and complexity of the biosensor and the associated methods of use.

Accordingly, herein provided is a biosensor for the detection of an analyte comprising:
a) i) a nucleic acid substrate coupled to a first support and a nucleic acid cleaving enzyme; or
  ii) a nucleic acid cleaving enzyme comprising a nucleic acid substrate coupled to a first support; and
b) a nucleic acid binding molecule coupled to a microzone on a second support;
wherein the nucleic acid substrate comprises a detection moiety;
wherein the nucleic acid enzyme is capable of cleaving the nucleic acid substrate;
wherein the nucleic acid cleaving enzyme is activated upon contact with the analyte, thereby cleaving the nucleic acid substrate to release a cleavage product comprising the detection moiety; and
wherein the nucleic acid binding molecule binds to the cleavage product.

In some embodiments, the nucleic acid cleaving enzyme is an RNA-cleaving DNAzyme, a DNA-cleaving DNAzyme, a ribozyme, or an endonuclease that has DNA and/or RNA cleaving activities. In some embodiments, the nucleic acid cleaving enzyme is an RNA-cleaving DNAzyme. In some embodiments, the nucleic acid cleaving enzyme is a DNA-cleaving DNAzyme. In some embodiments, the nucleic acid cleaving enzyme is a ribozyme. In some embodiments, the nucleic acid cleaving enzyme is an endonuclease. In some embodiments, the ribozyme is an allosteric ribozyme. In some embodiments, the ribozyme is an aptazyme.

The nucleic acid binding molecule can be any molecule that binds to a nucleic acid such as a cleavage product generated by the nucleic acid cleaving enzyme. The nucleic acid binding molecule includes another nucleic acid such as an oligonucleotide that is capable of hybridizing, i.e. specific non-covalent binding with a complementary, or partially complementary, with the nucleic acid sequence of the cleavage product. In some embodiments, the nucleic acid binding molecule is an oligonucleotide. In some embodiments, the nucleic acid cleaving enzyme is a DNAzyme and the nucleic acid binding molecule is an oligonucleotide. In some embodiments, the nucleic acid cleaving enzyme is an RNA-cleaving DNAzyme and the nucleic acid binding molecule is an oligonucleotide. In some embodiments, the oligonucleotide comprises DNA and/or RNA. In some embodiments, the oligonucleotide is RNA. In some embodiments, the oligonucleotide is DNA.

The analyte of the present disclosure can be any analyte that can activate the nucleic acid cleaving enzyme upon contact. For example, the analyte may be a metal ion, a small organic molecule, a small inorganic molecule, a drug, a hormonal growth factor, a biomolecule, a toxin, a biopolymer such as a nucleic acid, a carbohydrate, a lipid, a peptide, a protein, or a virus, a microorganism such as a bacterium, or a cell. In some embodiments, the analyte is a metal ion, a small organic molecule, a small inorganic molecule, a drug, a hormonal growth factor, a biomolecule, a toxin, a biopolymer, a virus, a microorganism, or a cell. In some embodiments, the biopolymer is a nucleic acid, a carbohydrate, a lipid, a peptide, or a protein. In some embodiments, the microorganism is a bacterium. In some embodiments, the bacterium is *Bacillus, Bartonella, Bordetella, Borrelia, Brucella, Campylobacter, Chlamydia, Chlamydophila, Clostridium, Corynebacterium, Enterococcus, Escherichia, Francisella, Haemophilus, Helicobacter, Klebsiella, Legionella, Leptospira, Listeria, Mycobacterium, Mycoplasma, Neisseria, Nocardia, Pseudomonas, Rickettsia, Salmonella, Shigella, staphylococcus, Streptococcus, Treponema, Ureaplasma, Vibrio*, or *Yersinia*. In some embodiments, the bacterium is *Escherichia coli*. In some embodiments, the bacterium is *Klebsiella pneumoniae*.

A strategy disclosed herein includes a biosensor that captures the cleavage product from a relatively large volume of solution onto a microzone on the second support, thereby enriching the concentration of the cleavage product. For example, the concentration of a cleavage product can be increase 1,000-fold when 1 mL of a cleavage product of about 5 nm is transferred to a microzone of 2 mm in diameter. In some embodiments, the microzone is about 0.5 mm to 5 mm in diameter. In some embodiments, the microzone is about 1 mm to 4 mm in diameter. In some embodiments, the microzone is about 1.5 mm to 3 mm in diameter. In some embodiments, the microzone is about 2 mm in diameter.

The first support can be any solid or semi-solid material that is capable of being coupled to the nucleic acid substrate and/or nucleic acid cleaving enzyme, for example, modified agarose beads, graphene oxide, gold nanoparticles or glass beads, whether by covalent or non-covalent immobilization chemistry. In some embodiments, the first support comprises modified agarose beads, graphene oxide, gold nanoparticles or glass beads. In some embodiments, the nuclei acid substrate and/or nucleic acid cleaving enzyme is coupled to the first support by covalent or non-covalent immobilization chemistry. In some embodiments, the first support comprises modified agarose beads, graphene oxide, gold nanoparticles or glass beads, and wherein the nucleic acid substrate and/or nucleic acid cleaving enzyme is coupled to the first support by covalent or non-covalent immobilization chemistry. In some embodiments, the immobilization chemistry comprises streptavidin, cyanuric chloride, isothiocyanate, nitrophenyl chloroformate, hydrazine, amino, thiol, acrydite, NHS ester activated, aldehyde, azlactone-activated, carbonyl diimidazole activated, maleimide, iodoacetyl-activated, or biotin chemistries.

The second support can be any solid or semi-solid material that is capable of being coupled to the nucleic acid binding molecule, for example, paper or a paper-based product, such as nitrocellulose, glass fiber substrate, graphene paper, modified agarose beads, graphene oxide, gold nanoparticles, or glass beads. The second support can also be backed with a plastic sheet, for example, the paper can be backed with a plastic sheet. Accordingly, in some embodiments, the second support comprises paper or a paper-based product, glass fiber substrate, graphene paper, modified agarose beads, graphene oxide, gold nanoparticles, or glass beads. In some embodiments, the paper or paper-based product is nitrocellulose.

The nucleic acid binding molecule may be coupled to the second support via covalent or non-covalent chemistries, by conjugating to molecules that bind to each other. For example, biotin is known to have affinity for binding to streptavidin. As such, an example of coupling is for the nucleic acid binding molecule to be conjugated to biotin, and the second support to be conjugated to streptavidin, so that the nucleic acid binding molecule and the second support are coupled via the binding between the biotin and the streptavidin. In some embodiments, the nucleic acid binding molecule is conjugated to biotin and the second support is conjugated to streptavidin, and the biotin is bound to the streptavidin.

For creating the microzone on the second support, a hydrophobic material such as wax or any other hydrophobic material that is generally impermeable to aqueous solutions can be used to create the microzone. In some embodiments, the microzone is created by hydrophobic material printing. In some embodiments, the microzone is created by wax printing.

The biosensor of the present disclosure includes a detection moiety for detection of presence of the analyte in a sample. The detection moiety can be coupled to the part of the nucleic acid substrate that is to be released upon contact with the analyte.

There are many available detection systems known to the person skilled in the art, who can identify any suitable fluorescent, colorimetric, chemiluminescent, or electrochemical detection moiety for use in a detection system. In some embodiments, the detection moiety is coupled to the part of the nucleic acid substrate that is to be released upon contact. In some embodiments, the detection moiety comprises a fluorescent, colorimetric, chemiluminescent, radio-labeled, or electrochemical moiety coupled to the part of the nucleic acid substrate that is to be released upon contact. In some embodiments, the detection system is a fluorescent detection system comprising a fluorescent moiety. In some embodiments, the fluorescent moiety is a fluorescein dye, cyanine dye, rhodamine dye, TYE™ dye, ATTO™ dye, Alexa Fluor® dye, or LI-COR IRDye®. In some embodiments, the fluorescein dye is fluorescein amidite (FAM). The skilled person would readily recognize the instrument for detecting the fluorescent moiety, for example, fluorescence imagers. In some embodiments, the fluorescent moiety is detected by a fluorescence imager. In some embodiments, the electrochemical moiety is methylene blue. In some embodiments, the nucleic acid substrate or cleavage product is modified to produce a detection moiety. In some embodiments, the nucleic acid substrate or cleavage product is chemically reacted to produce a detection moiety.

The skilled person would also readily recognize the components, such as enzymes, substrates, and color changing dye, for a biosensor that uses a colorimetric detection system, for example, as described in US20160047826A1, herein incorporated by reference. However, US20160047826A1 uses RCA for amplification of signal to increase sensitivity and does not concentrate signal in a microzone as presently disclosed. In some embodiments, the colorimetric detection system comprises an enzymatic moiety. In some embodiments, the enzymatic moiety comprises urease, alkaline phosphatase, horseradish peroxidase, glucose oxidase, or β-galactosidase. In some embodiments, the colorimetric detection system comprises a detection of pH change. In some embodiments, the pH is tested using litmus paper or dyes. In some embodiments, the pH is tested using a pH paper or meter. In some embodiments, the enzymatic moiety is a pH changing enzyme. In some embodiments, the pH changing enzyme comprises urease, and the substrate comprises urea, and the color changing dye comprises bromothymol blue, phenol red, neutral red, cresol red, m-cresol purple, or o-cresolphthalein complexone. In some embodiments, urease catalyzes the conversion of urea to ammonia, which increases the pH of the solution, which can then be detected by a change in color of the color changing dye.

The biosensor of the present disclosure is also capable of multiplexing for the detection of different analytes. Such a multiplexing biosensor may have one more additional nucleic acid substrates and/or one or more additional nucleic acid cleaving enzymes that are coupled to the first support or coupled to additional supports. These enzymes are activated upon contact with different, additional analytes, which leads to the production of additional specific cleavage products. The multiplexing biosensor can have on the second support multiple microzones that are defined regions each covered with a specific, additional nucleic acid binding molecule that binds to the additional specific cleavage products produce by the nucleic acid cleaving enzymes cleaving the nucleic acid substrates. Accordingly, in some embodiments, the biosensor further comprises i) one or more additional nucleic acid substrates coupled to the first support and one or more additional nucleic acid cleaving enzymes, or ii) one or more additional nucleic acid cleaving enzymes each comprising one of one or more additional nucleic acid substrates coupled to the first support, wherein each of the one or more additional nucleic acid substrates comprises a detection moiety; wherein each of the one or more additional nucleic acid cleaving enzymes is activated upon contact with one of one or more additional analytes, thereby cleaving the one or more additional nucleic acid cleaving enzymes to release one or more additional cleavage products comprising the detection moiety; wherein each of the one or more additional nucleic acid cleaving enzymes is specific to one of the one or more additional analytes; wherein each of the one or more additional nucleic acid cleaving enzymes is specific to one of the one or more additional nucleic acid substrates; wherein the biosensor further comprises one or more additional nucleic acid binding molecules, each of the one or more additional nucleic acid binding molecules binds to one of the one or more additional cleavage products; and wherein each of the one or more additional nucleic acid binding molecules is concentrated within one of one or more additional microzones on the second support. In some embodiments, each of the one or more additional microzone is between 0.5 mm to 5 mm in diameter.

The biosensor of the present disclosure is low cost, has high sensitivity and simple to use. Accordingly, also provided herein is a method for the detection of at least one analyte in a sample, the method comprising:

a) placing the biosensor of the present disclosure into a test solution comprising the sample;
b) retrieving the second support from the test solution; and
c) detecting the presence of the at least one analyte on the second support.

In some embodiments, the method further comprises after step b), washing the second support.

The method can be adapted for multiplexing detection. In some embodiments, the method further comprises i) one or more additional nucleic acid substrates coupled to the first support and one or more additional nucleic acid cleaving enzymes, or ii) one or more additional nucleic acid enzymes each comprising one of one or more additional nucleic acid substrates, and one or more additional nucleic acid binding molecules.

The skilled person can readily recognize the test solution can be any aqueous solution that is compatible for use of the biosensor. Because the microzone concentrate the cleavage product, the biosensor described herein can be used in a large volume of test solution, of up to 100 mL. In some embodiments, the test solution is up to about 100 mL. In some embodiments, the test solution is about 0.5 mL to 100 mL. In some embodiments, the test solution is about 1 mL to 100 mL. In some embodiments, the test solution is about 0.5, 1, 2, 3, 4, 5, 10, 15, 20, 25, 50, or 100 mL. The biosensor disclosed herein is sensitive, and can be used to detect an analyte such as a bacterium at a concentration down to 100 CFU/mL, or down 100 CFU in total. In some embodiments, the method detects down to about 100 CFU/mL. In some embodiments, the method detects down to 100 CFU in total. The washing can be carried out with any solution that does not interfere with the detection of the analyte, whether the detection uses a fluorescent, colorimetric, chemiluminescent, radiolabeled, or electrochemical detection system. In some embodiments, the detection comprises fluorescent, colorimetric, chemiluminescent, radiolabeled, or electrochemical detection. In some embodiments, the detection comprises colorimetric detection. In some embodiments, the colorimetric detection comprises an enzymatic moiety. In some embodiments, the enzymatic moiety comprises a pH changing enzyme. In some embodiments, the colorimetric detection comprises in c) exposing the second support to a solution containing a substrate and a color changing dye. In some embodiments, the pH changing enzyme comprises urease. In some embodiments, the substrate for the pH changing enzyme comprises urea. In some embodiments, the color changing dye comprises bromothymol blue, phenol red, neutral red, cresol red, m-cresol purple, or o-cresolphthalein complexone. In some embodiments, the color changing dye comprises phenol red. In some embodiments, the color changing dye is phenol red. In some embodiments, the pH changing enzyme is urease, the substrate is urea, and the color changing dye is bromothymol blue, phenol red, neutral red, cresol red, m-cresol purple, or o-cresolphthalein complexone. In some embodiments, the method comprises exposing the urease to urea, whereby the urease catalyzes the conversion of urea to ammonia, which increases the pH of the solution, which can then be detected by a change in color of the color changing dye.

Also provided is herein is a kit for detecting an analyte, wherein the kit comprises the biosensor of present disclosure, and instructions for use of the kit for detecting an analyte. In some embodiments, the kit comprises a biosensor having i) one or more additional nucleic acid substrates coupled to the first support and one or more additional nucleic acid cleaving enzymes or ii) one or more additional nucleic acid cleaving enzymes each comprising one of one or more additional nucleic acid substrates coupled to the first support, wherein each of the one or more additional nucleic acid cleaving enzymes is capable of being activated by one of one or more additional analytes, and one or more additional nucleic acid binding molecules. In some embodiments, the kit further comprises one or more of a) container, b) buffer, c) washing solution, d) wherein the detection system comprises i) substrate for an enzymatic moiety, ii) substrate for chemiluminescent detection, and/or iii) color changing dye. In some embodiments, the enzymatic moiety is a pH changing enzyme. In some embodiments, the pH changing enzyme comprises urease. In some embodiments, the substrate for the enzymatic moiety comprises urea. In some embodiments, the color changing dye comprises bromothymol blue, phenol red, neutral red, cresol red, m-cresol purple, or o-cresolphthalein complexone. In some embodiments, the pH changing enzyme is urease, the substrate is urea, and the color changing dye is bromothymol blue, phenol red, neutral red, cresol red, m-cresol purple, or o-cresolphthalein complexone.

The above description generally describes the present disclosure. A more complete understanding can be obtained by reference to the following specific Examples. These Examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

The following non-limiting examples are illustrative of the present disclosure:

Example 1: Materials and Methods

Synthesis and purification of oligonucleotides: All DNA and RNA-containing oligonucleotides were purchased from Integrated DNA Technologies (IDT, Coralville, Iowa, USA) and were purified via standard 10% denaturing (7 M urea) polyacrylamide gel electrophoresis (dPAGE). Their concentrations were determined spectroscopically. The sequences and functions of all synthetic oligonucleotides used herein are provided in Table 1.

TABLE 1

The sequences of and modifications to all oligonucleotides used in this disclosure [7].

| SEQ ID NO: | Name | Labels | Sequence (5'-3') | Note |
|---|---|---|---|---|
| 1 | EC1 | 3'-Biotin; 5'-FAM; R = riboA | CGTGT GTCAC AACTC TTCCT AGCTR TGGTT CGATC AAGAG ATGTG CGTTG TCGAG ACCTG CGACC GGAAC ACTAG ACTGT GTGGG GATGG ATTTC TTTAC AGTTG TGTG | DE1 + FS1 |
| 2 | DE1 | 3'-Biotin | GATGT GCGTT GTCGA GACCT GCGAC CGGAA CACTA CACTG TGTGG GGATG GATTT CTTTA CAGTT GTGTG | Part of EC1 |
| 3 | FS1 | 5'-FAM; R = riboA | CGTGT GTCAC AACTC TTCCT AGCTR TGGTT CGATC AAGA | Part of EC1 |
| 4 | UrEC1 | 3'-Biotin; 5'-urease; R = riboA | CGTGT GTCAC AACTC TTCCT AGCTR TGGTT CGATC AAGAG ATGTG CGTTG TCGAG ACCTG CGACC GGAAC ACTAG ACTGT GTGGG GATGG ATTTC TTTAC AGTTG TGTG | DE1 + UrS1 |
| 5 | UrS1 | 5'-NH$_2$; R = riboA | TTTTT CGTGT GTCAC AACTC TTCCT AGCTR TGGTT CGATC AAGA | Part of UrEC1 |
| 6 | LT1 | None | CAAGA CGCAC ATCTC TTGAT CGAAC C | Ligation template |
| 7 | FDNA1 | 5'-FAM | CGTGT GTCAC AACTC TTCCT AGCTA | Reference sequence |
| 8 | KP6 | 3'-Biotin; 5'-FAM; R = riboA; F = fluorescein-dT; Q = dabcyl-dT | TTTTT TTTTT TTCTA TGAAC TGACQ RFGAC CTCAC TACCA AGATG CCATC CTACC AACCA TGACT GGTTT GTACT AAGAG ATTTC AGGCA TCGCT GCACG TCGTA GGTGA GCTCT GAACT CG | DE2 + FS2 |
| 9 | DE2 | 3'-Biotin | ATGCC ATCCT ACCAA CCATG ACTGG TTTGT ACTAA GAGAT TTCAG GCATC GCTGC ACGTC GTAGG TGAGC TCTGA ACTCG | Part of KP6 |
| 10 | FS2 | 5'-FAM; R = riboA; F = fluorescein-dT, Q = dabcyl-dT | TTTTT TTTTT TTCTA TGAAC TGACQ RFGAC CTCAC TACCA AG | Part of KP6 |
| 11 | LT2 | None | GTTGG TAGGA TGGCA TCTTG GTAGT GAGGT C | Ligation template |
| 12 | CDS1 | 5'-Biotin | TTTTT TTAGC TAGGA AGAGT TGTGA CACAC G | Capture DNA 1 |
| 13 | CDS2 | 5'-Biotin | TTTTG TCAGT TCATA GAAAA AAAAA AAA | Capture DNA 2 |

Enzymes, chemicals and other materials: ATP, T4 DNA ligase, and T4 polynucleotide kinase (PNK), along with their respective buffers, were purchased from Thermo Scientific (Ottawa, ON, Canada). Nitrocellulose membrane (HF120), which was backed with a thin plastic layer on one side, was acquired from GE Healthcare, Canada. Streptavidin-coated agarose beads with a nominal diameter of 35 μm were obtained from TriLink Biotechnologies, Inc. Streptavidin from *Streptomyces avidinii*, urease powder from *Canavalia ensiformis* (Jack bean), maleimidobenzoic acid N-hydroxy-succinimide ester (MBS), and phenol red were obtained from Sigma-Aldrich (Oakville, ON, Canada). Water used in the experiments was purified with a Milli-Q Synthesis A10 water-purification system. All other chemicals were purchased either from Sigma-Aldrich or Bioshop Canada and were used without further purification.

Preparation of bacterial cells: *Escherichia coli* K12 (*E. coli* K12; MG1655) and *K. pneumoniae* (ATCC13883) which are regularly maintained in inventors' laboratory, were used. In order to measure the colony forming units (CFU/mL) of *E. coli* cells, a single colony freshly grown on Luria Broth (LB) agar plate was first taken, inoculated into 2 mL of LB and grown for 14 h at 37° C. with continuous shaking at 250 rpm. Following incubation, 10-fold serial dilution of bacterial culture was conducted and 100 μL of the diluted solutions was then spread onto LB agar plates (done in triplicate) and incubated at 37° C. for 16 h. Finally, the colonies were counted and averaged in order to obtain the number of CFU/mL. For preparation of bacterial samples for testing, 1 mL of each dilution was centrifuged at 11,000 g for 5 min at 4° C. The clear supernatant was then discarded, and the cell pellet was re-suspended in 100 μL of double-deionized water (ddH$_2$O) and heated at 65° C. for 5 min to release the DNAzyme-activating target. The heat-treated cell suspension was then vortexed to dissolve the cell pellet completely and stored at −20° C. The culturing and the test sample preparation of *K. pneumoniae* were conducted using the same protocol described above except for the use of *K. pneumoniae* bacteria to replace *E. coli* bacteria.

Preparation of EC1: EC1 was prepared by T4 DNA ligase mediated DNA ligation of DE1 and FS1 in the presence of LT1 as the template. The sequences used are provided in Table 1. In brief, 2 nmol of DE1 was phosphorylated in 200 μL of 1×PNK buffer A containing 2 mM ATP (final concentration) with 40 U (units) of PNK enzyme at 37° C. for 40 min. The reaction was quenched by heating the mixture at 90° C. for 5 min. Then an equal number of FS1 and LT1 were added to the reaction mixture. The mixture was then heated at 90° C. for 2 min before being cooled for 15 min until it reached room temperature. Once the mixture had cooled, 40 μL of 10×DNA ligase buffer and 40 U of T4 DNA Ligase were added and the final volume was adjusted to 400 μL by adding ddH$_2$O. After incubation at room temperature for 2 h, the DNA molecules were isolated by ethanol precipitation and the ligated DNA molecules were purified via 10% dPAGE. After being dissolved in ddH$_2$O, the DNAzyme concentration was measured using a DeNovix DS-11+Spectrophotometer and adjusted to 1 μM via dilution in ddH$_2$O. Finally, the DNAzymes solutions were stored at −20° C. until use in the experiments.

Preparation of KP6: KP6 was also prepared by T4 DNA ligase mediated DNA ligation of DE2 and FS2 in the presence of LT2 as the template using a similar protocol as described in "Preparation of EC1" above. The sequences used are provided in Table 1.

Preparation of UrEC1: UrEC1 was prepared by conjugating 5′-NH$_2$-EC1 and urease via the bifunctional linker maleimidobenzoic acid N-hydroxy-succinimide ester (MBS) according to a previously reported method [8,9] NH$_2$-EC1 was prepared by ligating DE1 to UrS1 using the same protocol described in "Preparation of EC1" above. An MBS solution (6.4 mM) was made by dissolving 2 mg MBS (6.4 μmol) in 1 mL of dimethyl sulphoxide (DMSO). Similarly, a urease solution was produced by dissolving 1.5 mg urease (3.3 nmol) powder in 1 mL of 1×PBS buffer (pH 7.2). 1 nmol NH2-DNAzyme and 3.2 μL of the MBS solution (20 nmol) were mixed and adjusted to a final reaction volume of 100 μL with 1×PBS buffer, and allowed to react at room temperature. After 2 h, the mixture was passed through a membrane-based molecular sizing centrifugal column with a molecular weight cut-off of 3,000 Daltons (NANOSEP OMEGA, Pall Incorporation) in order to remove excess MBS. The column was washed with 50 μL of 1×PBS buffer 3 times, and the DNAzyme was resuspended in 100 μL of 1×PBS buffer. The urease solution (1 mL, 3.3 nmol) was then added to the MBS activated DNAzyme. The conjugation reaction was allowed to proceed at room temperature for 4 h. The mixture was filtered through a 300,000-Dalton cut-off centrifugal column. The UrEC1 conjugate was then washed with 50 μL of 1×PBS buffer 3 times and resuspended in 100 μL of 1×PBS buffer. Its concentration was quantified based on previous developed method [10]

Preparation of EC1-SAB (EC1 conjugated to streptavidin-coated agarose beads): In a 1.5 mL microfuge tube, 20 μL of streptavidin-coated agarose beads were washed with 100 μL of 1× reaction buffer (1×RB; 50 mM HEPES, pH 7.5, 150 mM NaCl, 15 mM MgCl$_2$). After centrifugation, the clear supernatant was discarded, and 10 μL of beads remained in the tube. 5 pmol of the biotinylated DNAzyme (5 μL of 1 μM), 50 μL of 2×RB and 35 μL of ddH$_2$O were then added to the 10 μL of washed beads to make 100 μL of total reaction volume. After 1 h incubation at room temperature, the tube was centrifuged in order to remove free DNAzymes. After wash four times with 100 μL of 1×RB, the immobilized DNAzymes on the beads were ready for use in the cleavage test.

Preparation of KP6-SAB (KP6 conjugated to streptavidin-coated agarose beads): This conjugate was prepared using the same protocol described in "Preparation of EC1-SAB (EC1 conjugated to streptavidin-coated agarose beads)" except for the use of KP6 to replace EC1.

Preparation of P$^C$DNA (paper sensor with capture DNA): To achieve the stable immobilization of capture DNA (the complementary sequence to the cleavage fragment) on the nitrocellulose (NC) membrane, streptavidin was used to bind the biotinylated capture DNA. Briefly, in 300 μL of total reaction volume, 1 nmol of the biotinylated capture DNA and 30 μL of 2 mg/mL streptavidin were mixed in the final concentration of 1×PBS buffer. After 2 h incubation at room temperature, the mixture was filtered through a 10,000-Dalton cut-off centrifugal column (NANOSEP OMEGA, Pall Incorporation) by centrifugation at 5,000 g for 10 min to remove free capture DNA. The capture DNA-streptavidin conjugate was resuspended and collected from the filter in two aliquots of 40 μL of 1×PBS buffer for a final collected volume of ~80 uL. The concentration of the capture DNA-streptavidin conjugate was estimated to be 12.5 μM. The wax-printing technique was used (using a Xerox ColorQube 8570N solid wax printer) to produce microzones on paper measuring 2 mm in diameter to achieve consistent experimental results. 2 μL of the above solution (capture DNA-streptavidin conjugate) was then deposited onto each microzone and allowed to dry at room temperature. The paper was then immersed in 1×PBS buffer (containing 5% Skim milk and 0.01% (v/v) Tween 20) for 20 min to block the paper and prevent the attachment of the cleavage fragments to undesired sites of the paper. After washing 2 times with 1×PBS buffer and drying at room temperature, the paper was used in the experiments.

Fluorescence-based *E. coli* detection with P$^C$DNA: P$^C$DNA, which contained the capture DNA CDS1, was used to concentrate the cleavage fragment of EC1. Upon cleavage, the FAM-labeled cleavage fragment of EC1, named FDNA1, is released from the beads and hybridized to CDS1 on P$^C$DNA. The fluorescence signal on the paper, indicating the presence of the target bacteria in the sample, can then be interpreted by a non-expert using a simple hand-held fluorescence device. Briefly, after the preparation of EC1-SAB (as described in "Preparation of EC1-SAB (EC1 conjugated to streptavidin-coated agarose beads)", 500 µL of 2×RB and a *E. coli* sample prepared from the number of cells needed for each experiment were added to EC1-SAB. The final volume of the mixture was adjusted to 1 mL by adding ddH$_2$O. The as-prepared P$^C$DNA was placed inside the reaction mixture at the beginning of the reaction. After incubation at room temperature for 2 h with continuous shaking, the paper strip was taken out and washed by immersing into 5 mL of 1×PBS buffer before being scanned with a Chemidoc™ fluorescence imager. The fluorescence signal of the paper was then analyzed by ImageJ Software.

Time-dependent study of the fluorescence signal increase on P$^C$DNA. To evaluate the hybridization time of the cleavage fragment FDNA1 with P$^C$DNA, two experiments were conducted. In the first experiment, the hybridization time of the fully cleaved EC1 was assessed, and to this end, the DNAzyme cleavage reaction and hybridization of the cleavage product with P$^C$DNA were conducted in two separate steps (FIG. 2A). Briefly, after immobilizing 5 pmol of the biotinylated DNAzyme onto the surface of agarose beads as describe above, the cleavage reaction was conducted in 1 mL of 1×RB at room temperature for 2 h with 10$^7$ CFU/mL of *E. coli* cells. A separate reaction mixture was prepared for each time point specified in FIG. 2A. Following 2 h cleavage reaction, P$^C$DNA was placed inside each reaction mixture. The paper from each sample was taken out at the time points specified in FIG. 2A and immersed into 5 mL of 1×PBS buffer before being scanned with a Chemidoc™ fluorescence imager. In the second experiment, however, both cleavage and hybridization reactions were conducted as a one-pot reaction (FIG. 2B), and P$^C$DNA was placed inside each reaction mixture at the beginning of the cleavage reaction as described in "Fluorescence-based *E. coli* detection with P$^C$DNA". A separate reaction mixture was prepared for each time point, and at that time point P$^C$DNA was taken out before being immersed into 5 mL of 1×PBS buffer and scanned with a Chemidoc™ fluorescence imager.

Sensitivity test with P$^C$DNA: A wax-printed paper with eight reference zones (as illustrated in FIG. 3A) was used as a reference tool for determining the concentration of *E. coli* in a test sample. A specific amount of chemically synthesized FDNA1 was deposited onto each reference zone, and the signal level of each zone is carefully calibrated to the expected signal from the amount of FDNA1 produced from EC1-SAB by a specific concentration of *E. coli* (CFU/mL) and hybridized onto P$^C$DNA. To evaluate the detection sensitivity of P$^C$DNA, different concentrations of *E. coli* cells were used. The test samples were prepared from *E. coli* cultures containing 10$^7$, 10$^6$, 10$^5$, 10$^4$, 10$^3$, 10$^2$, 10, and 1 CFU/mL as described in "Preparation of bacterial cells". Each cell dilution was then subjected to the fluorescence-based assay described in "Fluorescence-based *E. coli* detection with P$^C$DNA". After incubation at room temperature for 2 h with continuous shaking, P$^C$DNA was taken out and washed by immersing into 5 mL of 1×PBS buffer. The paper from each sample was then placed at the middle of the reference paper (Test zone in FIG. 3A) and scanned with a Chemidoc™ fluorescence imager. The fluorescence signal of each test zone was then quantified using ImageJ Software, and plotted against concentration of *E. coli* to determine the detection sensitivity of the paper-based fluorescent assay.

Multiplex detection of *E. coli* and *K. pneumoniae* with a 2-plex P$^C$DNA: The required 2-plex P$^C$DNA was prepared according to the same protocol described in "Preparation of P$^C$DNA (paper sensor with capture DNA)" except that two different capture DNA oligonucleotides, CDS1 and CDS2 (see Table 1 for sequence information) were used to create two capture zones as illustrated in FIG. 4B. Two DNAzymes were used: the *E. coli*-specific DNAzyme EC1, and the *K. pneumoniae* (KP)-specific DNAzyme KP6. 5 pmol of each biotinylated DNAzyme was immobilized onto the surface of streptavidin-coated agarose beads as described in "Preparation of EC1-SAB (EC1 conjugated to streptavidin-coated agarose beads)". These bead-immobilized DNAzymes (EC1-SAB and KP6-SAB) were then mixed together and used in the cleavage tests with the samples containing either *E. coli*, *K. pneumoniae*, or both as specified in FIG. 4B. The assay procedure was similar to the one described in "Fluorescence-based *E. coli* detection with P$^C$DNA" above. 10$^6$ CFU/mL of bacterial cells were used in these experiments.

P$^C$DNA-based colorimetric assay: The cleavage reaction and detection procedure were conducted in the same manner as described for the fluorescent-based assay in "Fluorescence-based *E. coli* detection with P$^C$DNA", the only two differences were: 1) the use of UrEC1-SAB to replace EC1-SAB, and 2) after the cleavage reaction, the urease-tagged cleavage fragment of the DNAzyme, UrDNA, is hybridized to P$^C$DNA. Briefly, after incubation of UrEC1-SAB with *E. coli* for 2 h with P$^C$DNA inside the tube, the paper was taken out and immersed into 5 mL of 1×PBS buffer followed by washing with acetic acid buffer (0.1 mM, pH 5.5). Then, a mixture containing 1.6 µL of acetic acid buffer (0.1 mM, pH 5.5), 0.4 µl of 0.04% phenol red and 2 µL of a urea-containing solution (3 M NaCl, 60 mM MgCl2, 50 mM urea, pH 5.5) was added onto the test zone for litmus test. In this assay, the color transition from yellow-to-pink on the paper, which is due to the hydrolysis of urea and evaluation of the solution pH, indicates the presence of the target bacteria in the sample and can be detected by the naked eye. For quantifying the color intensity on the paper, after a signal producing time of 10 min, the paper sensors were photographed and images were sent to a computer. Using ImageJ software, the image of the papers was split into its color channels. The green color channel which is the complimentary color of red (the reaction's endpoint color) was then selected and inverted. The color intensity of each test zone was then quantified and plotted against concentration of *E. coli* cells in the sample to quantify the detection sensitivity of the paper-based colorimetric assay (FIG. 8A).

Solution-based colorimetric assay: The same experiments were conducted as the paper-based colorimetric assay described above, only this time without the use of P$^C$DNA inside the reaction mixtures. After incubation of UrEC1-SAB with *E. coli* cells for 2 h, the samples were centrifuged to separate the cleavage fragments from uncleaved DNAzymes on beads. 10 µL of the clear supernatant was then transferred into a new reaction tube followed by a 10-fold dilution with ddH$_2$O to minimize the impact of the buffering agent on the reporting reaction. A mixture containing 80 µL of acetic acid buffer (0.1 mM, pH 5.5), 20 µl of 0.04% phenol red and 100 µL of a urea-containing solution (3 M NaCl, 60 mM MgCl2, 50 mM urea, pH 5.5) was then added to the diluted cleavage solution. Note that this reaction solution should have a starting pH of 5.5; at this pH value, phenol red exhibits a yellow color. After a signal producing time of 1 h, the samples were photographed and the absorbance of the reactions at 570 nm and 443 nm (A570 and A443) was measured using a microplate scanning spectrometer (TECAN M1000). A570/A443 was then plotted against concentration of E. coli in the sample to quantify the detection sensitivity of the solution-based colorimetric assay (FIG. 8B). This measurement was performed due to the fact that the color of phenol red exhibits a gradual transition from yellow ($\lambda$max=443 nm) to red ($\lambda$max=570 nm) when the pH of a test solution changes from acidic to basic.

Performance of the P$^C$DNA test in different sample volumes: To evaluate the effect of the sample volume on hybridization time of the cleavage fragments to capture DNAs on the paper, samples with different volumes, as specified in FIG. 6, were subjected to the fluorescent-based assay described above. Briefly, for all sample volumes, after immobilizing 5 pmol of the biotinylated DNAzyme on the surface of agarose beads as describe earlier, the cleavage reaction was conducted at room temperature for 2 h with $10^7$ CFU/mL of E. coli cells. Each sample was adjusted to its final reaction volume by adding 1×RB. Following 2 hr incubation, the as-prepared P$^C$DNA was placed inside each reaction mixture. Note that a separate reaction mixture was prepared for each time point specified in FIG. 6A. The paper from each sample was taken out at certain time points and immersed into 5 mL of 1×PBS buffer before being scanned with a Chemidoc™ fluorescence imager.

Performance of the P$^C$DNA test in complex sample matrices: The performance of the P$^C$DNA test was evaluated with E. coli spiked into drinking water, apple juice, and milk samples (FIG. 9). First, the pH of the apple juice was adjusted to 7.5 using 0.2 M NaOH, while the milk and drinking water were directly used in the experiment without further treatment. The test samples were spiked with the E. coli sample to produce a final cell concentration of $10^5$ CFU/mL; for the controls, on the other hand, the samples were not spiked with E. coli. The samples were then subjected to the both fluorescent-based assay using EC1-SAB and colorimetric-based assay using UrEC1-SAB as described above.

Theoretical calculation of the local concentration of fluorogenic molecules on the paper microzones: The DNAzyme concentration in the solution is 5 nM (5 pmol of DNAzyme in 1 mL solution). According the manufacturer, HF 120 nitrocellulose membranes have a thickness of 135 μm and a porosity of ~70%. The volume of liquid in a 2 mm diameter region of the membrane is equal to $$0.70 \times \pi r^2 \times 135 \times 10^{-6} = 2.97 \times 10^{-10} \text{ m}^3$$

If all the DNA present in 1 ml ($1 \times 10^{-6}$ m$^3$) of solution is totally captured within the pores of a 2 mm microzone, then the concentration factor is equal to ratio of the volumes $$(1 \times 10^{-6})/(2.97 \times 10^{-10}) = 3370.$$

The estimated concentration of DNA in the microzone is then 5×3370=16,850 nM or 16.85 μM.

Rolling circle amplification (RCA) reaction: 500 μL of 2×RB and a relevant CIM of E. coli were added to EC1-SAB (containing 5 pmol of EC1). The final volume of the mixture was adjusted to 1 mL by adding ddH$_2$O. After incubation at room temperature for 120 minutes, 30 μL of the supernatant containing the cleavage fragment of EC1 was mixed with 1 μL of PNK (10 U μL$^{-1}$) and incubated at 37° C. for 30 min. The RCA reaction was then initiated by the addition of 1 μL of circular template, 1 μL of 129DNA polymerase (10 U μL$^{-1}$), 5 μL of dNTPs (10 mM), 5 μL of 10×RCA reaction buffer (330 mM Tris-acetate, 660 mM K-acetate, 100 mM Mg-acetate, 1% tween 20, 10 mM DTT, pH 7.9), 5 μL of 10×SYBR Gold and 2 μL of water. These reactions were carried out in a microplate scanning spectrometer (TECAN M1000) set to a constant temperature of 30° C. Fluorescence intensities were collected after 120 min of incubation.

Example 2. Validation of the Surface-to-Surface Product Enrichment (S2SPE) Sensing Strategy The Surface-to-Surface Product Enrichment (S2SPE) sensing method, illustrated in FIG. 1A, is a simple, two-step process. The first step is a one-pot reaction that accomplishes target binding, DNAzyme cleavage, and production enrichment onto the paper surface. In this step, EC1-SAB and P$^C$DNA are placed in a test tube containing the activating target from E. coli. The target molecule binds EC1 on the SAB, triggering the cleavage reaction and release of the FAM-labeled cleavage fragment (named FDNA1) from the SAB. The FDNA1 hybridizes with the P$^C$DNA, resulting in the beads-to-paper product enrichment. This is followed by the second step, in which the P$^C$DNA is retrieved, washed, and imaged. An advantage of this design is the concentration of FDNA1 from a relatively large volume of solution to a small microzone. A calculation (see above in Example 1) suggests that the FDNA1 concentration can be increased by ≈$10^3$-fold when 1 mL of 5 nm FDNA1 solution is transferred to a microzone of 2 mm in diameter. An additional advantage is that the approach eliminates background interferences from the sample because the sensor is taken out from the reaction mixture and washed, thus augmenting the signal-to-noise ratio for sensitive detection. To validate the proposed S2SPE sensing idea, the following reactions were performed. EC1-SAB (reaction i) or EC1 (reaction ii) was incubated in reaction buffer only with and without P$^C$DNA. EC1-SAB (reaction iii) or EC1 (reaction iv) was incubated in reaction buffer containing E. coli with and without P$^C$DNA (see "Preparation of bacterial cells" and "Fluorescence-based E. coli detection with P$^C$DNA" for detail). As shown in FIG. 1B, when free EC1 was used, a fluorescence signal was observed on the P$^C$DNA both in the absence and in the presence of E. coli (reactions ii and iv, respectively). This was to be expected because both the cleavage fragment and intact EC1 are able to move freely and to hybridize with P$^C$DNA. In contrast, when EC1-SAB was used, fluorescence was observed on the paper sensor only when E. coli was present but was not observed when E. coli was absent, thus signifying that immobilizing EC1 on SAB prevents uncleaved EC1 from hybridizing to the P$^C$DNA. These results highlight the importance of employing a solid support, such as beads, in the assay. It should be noted that large beads were used for two reasons. Firstly, because of their large size the beads are not entrapped within the paper pores (2-4 μm in diameter, much smaller than the bead size of 35 μm in diameter). Secondly, larger beads are associated with bigger drag force that pushes the beads away from the surface when the P$^C$DNA is washed. The drag force acting on a particle in a fluid increases with the diameter of the particle, as well as with an increase in the velocity of the fluid relative to the particle (washing increases the velocity of the fluid) [9]. Due to the size of beads used, it was easy to remove particles from the surface of the paper simply by washing.

DNA sequences from the above reactions were analyzed by 10% denaturing (7 m urea) polyacrylamide gel electrophoresis (dPAGE). From FIG. 1C, it is shown that the cleavage fragment FDNA1 was only found in the cases of reactions iii and iv, in which *E. coli* was present. In that of reaction ii, which used free (not bead-bound) EC1, only uncleaved EC1 was found in the supernatant; this confirmed that the fluorescence signal on P$^C$DNA for this mixture was due to the hybridization of the uncleaved EC1 with the capture DNA. In contrast, in the case of reaction i, which used EC1-SAB, no fluorescence signal was observed on the P$^C$DNA because no cleavage had occurred. More importantly, on comparing the intensity of the FDNA1 band from the iii–P$^C$DNA reaction with that of the iii+P$^C$DNA reaction, it is shown that the DNA capture process is efficient (94% of FDNA1 was transferred from the reaction solution to P$^C$DNA).

It was predicted that the reaction rate of the S2SPE assay would be dependent both on the cleavage rate of the DNAzyme and on the rate of hybridization between FDNA1 and CDS1. To investigate how these rates compare, time-dependent studies were conducted under two different sets of conditions: 1) the EC1 cleavage reaction and the FDNA1/P$^C$DNA hybridization reaction were performed separately (top images in FIG. 2A; specifically, EC1-SAB was incubated with the test sample for 2 h to induce full cleavage of EC1, followed by the hybridization reaction with P$^C$DNA for the indicated time periods), and 2) the cleavage and hybridization reactions were conducted as a one-pot reaction (bottom images in FIG. 2A).

FIG. 2B shows the time-dependent fluorescence intensities observed with the P$^C$DNA for the two above scenarios. A signal was observed within 1 min of the start of the reaction in the first test, whereas 5 min were required to produce a similar level of signal in the second test. The difference between the two tests decreased as a function of time and was very small after an incubation time of 2 h (FIG. 2B). These results show that the hybridization between FDNA1 and P$^C$DNA is quite efficient and that the cleavage reaction is the rate-limiting step. Therefore, the speed of the test is largely dependent on the cleavage activity of the DNAzyme. To simplify the experimental procedure and yet still reach the full potential of signal generation, the cleavage reaction and the hybridization reaction were performed as a one-pot reaction for 2 h for the remaining experiments.

Additional experiments were conducted to evaluate the effect of the sample volume on the hybridization rate of FDNA1 and P$^C$DNA (FIG. 6). In these experiments, paper strips of the same size, with the same size of microzone covered with the same amount of capture DNA, were incubated with the same amount of DNAzyme-bearing beads in the increasing reaction volume. As expected, lower hybridization rates were observed as the sample volume increased. This is because the DNA hybridization reaction is dependent on the FDNA1 concentration in solution. Inspection of FIG. 6 also shows that a fluorescence signal was detectable for all samples, with volumes ranging from 0.1 to 100 mL. This observation shows that the S2SPE assay is able to work with very large sample volumes, which is useful for many practical applications in which the detection of pathogenic bacteria has to be conducted with large sample volumes. In contrast, published methods for *E. coli* detection typically use small sample volumes in the 10-100 µL range (see Table 2 for a comparison of the presently disclosed method with other methods reported in the literature).

TABLE 2

Comparison of the S2SPE method to the published methods for *E. coli* detection.

| Method | Sensor Type Fluorescence and | Detection Limit[a] | Detection Reaction Volume[a] 1 mL (Up to | Ref. |
|---|---|---|---|---|
| S2SPE method | colorimetric | 100 CFU/mL | 100 mL) | |
| Literature methods | | | | |
| DNAzyme-based | fluorescence | 2 × 10$^5$ CFU/mL | 50 µL | [11] |
| DNAzyme-based | colorimetric | 2.5 × 10$^4$ CFU/mL | 180 µL | [8] |
| DNAzyme-based; RCA-based | fluorescence | 10 CFU/mL | 50 µL | [12] |
| DNAzyme-based; RCA-based | fluorescence | 10 CFU/mL | 50 µL | [13] |
| DNAzyme-based; graphene-based | fluorescence | 10$^5$ CFU/mL (CEM) | 150 µL | [14] |
| DNAzyme-based; DNA superstructure-based Paper-based; | fluorescence | 10$^4$ CFU/mL | 15 µL | [15] |
| DNAzyme-based; paper-based | fluorescence | 10$^4$ CFU/mL | 10 µL | [16] |
| Aptamer-based; chip-based | electrochemical | 2 × 10$^4$ CFU/mL | Not mentioned | [17] |
| Aptamer-based | colorimetric | 104 CFU/mL | 50 µL | [18] |
| Aptamer-based; quartz crystal microbalance | piezoelectric | 7.3 × 103 CFU/mL | 200 µL | [19] |
| PCR-based | fluorescence | 103 CFU/mL | 25 µL | [20] |
| RT-PCR-based | fluorescence | 6.4 × 103 CFU/mL | 50 µL | [21] |
| Antibody-based; flow-based | SPR | 100-1000 CFU/mL | 1 mL/min 2 mL (2 min flow) | [22] |

TABLE 2-continued

Comparison of the S2SPE method to the published methods for E. coli detection.

| Method | Sensor Type Fluorescence and | Detection Limit[a] | Detection Reaction Volume[a] 1 mL (Up to | |
|---|---|---|---|---|
| S2SPE method | colorimetric | 100 CFU/mL | 100 mL) | Ref. |
| Literature methods | | | | |
| Antibody-based; flow-based | electrochemical | $3 \times 10^4$ CFU/mL | 0.2 mL/min 8 mL (40 min flow) | [23] |
| Antibody-based; flow-based | electrochemical | $1.7 \times 10^5$ CFU/mL | 0.18 mL/min 7.2 mL (40-min flow) | [23] |
| Antibody-based; ELISA | absorbance | $10^3$ CFU/mL | 100 µL | [24] |
| Antibody-based; graphene-based | electrochemical | $10^3$ CFU/mL | 1 µL | [25] |

[a]Parameters better than the S2SPE method are shown in the bold text

Example 3: Semiquantitative Analysis Capability of the S2SPE Assay

The capability of the S2SPE assay for semiquantitative analysis was examined by preparing a wax-printed paper plate containing multiple reference zones, as shown in FIG. 3A. These reference zones were printed with specific amounts of FDNA1 that would be generated by 1 mL of *E. coli* cells at concentrations of 1-$10^7$ CFU mL$^{-1}$. Therefore, the bacterial concentration in a test sample should be quantifiable simply by comparing the signal intensities of the test and reference zones. Samples containing varying concentrations of *E. coli* (ranging from 1-10' CFU mL$^{-1}$) were prepared and incubated with EC1-SAB and P$^C$DNA. After 2 h of incubation with use of the one-pot reaction conditions, the P$^C$DNA was taken out and washed. The entire reference paper and test paper were scanned with a fluorescence imager. It is shown from FIG. 3B and FIG. 3C that this method is able to detect *E. coli* at concentrations as low as 100 CFU mL$^{-1}$; this is 100 times better than the gel-based assay, as shown in FIG. 3D. These results suggest that the S2SPE sensing method can be used to achieve semiquantitative analysis of *E. coli* with excellent detection sensitivity. For a direct comparison with an enzymatically based sensing method, an RCA was performed to amplify the cleavage product of EC1. In this assay, EC1-SAB was first incubated with varying numbers of *E. coli* CFUs in a reaction volume of 1 mL (the typical reaction volume for the S2SPE method). After 2 h incubation, 3% of each reaction solution was directly taken to make a 50 µL RCA reaction mixture (a typical RCA reaction). These RCA reactions were conducted for 120 min in the presence of SYBR Gold, followed by fluorescence measurement. The data are presented in FIG. 7. This method was able to detect $10^4$ cells—a performance similar to that of a gel-based assay, but 100 times worse than that of the S2SPE method. The result further illustrates an advantage of the S2SPE method: enhanced detection sensitivity as the result of enriching the cleavage fragment from a relatively large volume of solution to a small microzone. Table 2 also provides a comparison of the detection sensitivity of the presently disclosed S2SPE method and of the published enzymatic and nonenzymatic methods for *E. coli* detection. From the comparison it is shown that the S2SPE method, which uses product enrichment rather than enzyme amplification, is capable of better sensitivity than nearly all the reported nonenzymatic and enzymatic methods.

Example 4: Potential of S2SPE for Multiplex Detection

To demonstrate the potential of the S2SPE assay to perform multiplex detection, a duplex S2SPE assay was performed with two different RNA-cleaving DNAzyme compounds: EC1 and KP6, a recently reported RNA-cleaving DNAzyme for *K. pneumoniae* [26]. These two RNA-cleaving DNAzymes were chosen for the duplex assay because each RNA-cleaving DNAzyme was specifically activated by its cognate bacterium but did not exhibit cross-activity for the untargeted bacterium, as shown by dPAGE (FIG. 8). As discussed above, the cleavage of EC1 produces a fluorescent DNA product named FDNA1. KP6 behaves in the same way: when it is cleaved it also produces a fluorescent DNA product, named FDNA2. Note, however, that FDNA1 and FDNA2 have completely different sequences, and therefore a new capture DNA sequence, CDS2, was used to capture FDNA2. To prepare the needed sensing materials, EC1 and KP6 were first immobilized onto agarose beads separately, and these were subsequently mixed to produce the EC1/KP6-SAB mixture. A duplex P$^C$DNA sensor was also prepared that contained three microzones: an EC zone with CDS1 to capture FDNA1, a KP zone containing CDS2 to capture FDNA2, and the control zone with no capture DNA. Upon cleavage, FDNA1 and/or FDNA2 were released from the beads and captured by their corresponding zones (FIG. 4A). The results shown in FIG. 4B indicated that the duplex P$^C$DNA sensor performed as expected: each sensing zone demonstrated an increase in fluorescent when the target bacterial species was present in the test sample, but did not demonstrate any increase in fluorescence in the absence of the target bacteria. This experiment indicates that the S2SPE sensor is capable of detecting multiple targets in a single reaction with the aid of multiple RNA-cleaving DNAzymes.

Example 5: Colorimetric Detection

The S2SPE strategy was further modified to achieve colorimetric detection by using a urease-mediated litmus test

[5d, 27]. The design principle, with EC1 as the DNAzyme, is illustrated in FIG. 5A. EC1 is tagged with urease (Ur, to replace the FAM label in the fluorescence assay), and the conjugate, named UrEC1, is immobilized on the SAB to produce the sensing construct UrEC1-SAB. Upon cleavage induced by E. coli, the Ur-containing cleavage fragment (UrDNA) is released from the beads and captured by $P^CDNA$. The paper strip is then retrieved, washed, and exposed to a solution containing urea and phenol red (with a starting pH of 5.5). The urease in the microzone then hydrolyzes the urea to produce ammonia, raising the pH of the solution. This is reported by phenol red. The dye exhibits a yellow color at pH 5.5 but the color changes to red when the pH of the solution is elevated to pH 7 or higher.

As shown in FIG. 5B, after 10 min of color development, a gradual color transition from yellow to pink (right to left) was observed on the $P^CDNA$ sensor when the concentration of E. coli was serially increased (0-$10^7$ CFU m$L^{-1}$). The color change can easily be detected with the naked eye in cases of E. coli samples containing 100 CFU m$L^{-1}$ or above. This level of sensitivity is similar to that of the fluorescence-based detection method described earlier. With ImageJ analysis, the detection limit decreases to 10 CFU m$L^{-1}$ (FIG. 9A). The sensitivity of this method was also compared with that of a solution-based assay that tested the supernatant containing released UrDNA (FIG. 5C and FIG. 9B). The S2SPE method delivered 100-fold better sensitivity and required a sixfold shorter response time (10 min for S2SPE vs. 60 min for solution-based assay), due to the product enrichment. The colorimetric assay is best suited for field applications because the color change that occurs on the paper can be easily detected by the naked eye and does not require specialized equipment. The S2SPE assay also worked well with complex real-world samples, including drinking water, apple juice, and milk (FIG. 10A and FIG. 10B). Because the $P^CDNA$ is retrieved from the test sample and washed before signal production and detection, it is highly effective in minimizing background interferences associated with these complex sample matrices. Previously reported methods for detection of E. coli in complex samples required either sample dilution to minimize the effect of the background fluorescence in the fluorescent assay [28] or long incubation times for color development in the colorimetric assay [5d]. These requirements are not necessary in the S2SPE assay, because the cleavage product is isolated from sample matrix and concentrated on a surface that can be easily washed.

In summary, a simple but effective strategy for the design of ultrasensitive biosensors has been developed. The system makes use of a nucleic acid cleaving enzyme such as an RNA-cleaving DNAzyme, which produces two DNA fragments one of which is the cleavage product. Tethering of the enzyme onto micrometer-sized beads allows the cleavage fragment carrying the signal transducer to be enriched in a miniscule sensing zone (millimeter in diameter) on a paper strip immersed in the reaction solution, thus concentrating the signal transducer by three orders of magnitude. This surface-to-surface product enrichment strategy permits the design of a highly sensitive biosensing system with signal amplification. To the best of inventors' knowledge, this is the first report of high detection sensitivity being achieved through enrichment of reaction products of recognition elements of any kind. It is noteworthy that DNA/DNA hybridization has been widely used in methods to detect nucleic acid targets; however, although the S2SPE method also takes advantage of the DNA/DNA hybridization principle, without wishing to be bound by theory, it is significantly different in at least three aspects: 1) it uses a functional nucleic acid to detect an analyte such as a non-nucleic acid target, 2) it uses hybridization to enrich the product of a reaction, and 3) it uses a very low-cost paper device as the sensing platform. It has also been demonstrated that the S2SPE method is capable of simultaneously detecting two different bacterial pathogens—E. coli and K. pneumoniae—through the use of two different RNA-cleaving DNAzymes. The work from this disclosure should be easily extendable to any target-activated RNA-cleaving DNAzyme or any cleavage-based nucleic acid system. Therefore, the approach of this disclosure provides a new platform on which to build a large variety of sensors, given that many existing cleavage-based nucleic acid systems are available [29] and that a new cleavage-based nucleic acid system can be easily derived for a new target of interest through in vitro selection [4]. The system should be compatible with multiple signal transduction mechanisms, two of which—fluorescence and colorimetric reporting—have been demonstrated herein. Because the paper sensor can be retrieved from the test solution and simply washed before the detection assay, the approach also minimizes the impact of noise present in the complex sample matrices. In addition, the ability to tailor the system to generate a colorimetric signal without the need for special equipment makes it ideally suited for field applications, particularly in developing areas of the world.

While the present disclosure has been described with reference to examples, it is to be understood that the scope of the claims should not be limited by the embodiments set forth in the Examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

FULL CITATIONS FOR DOCUMENTS REFERRED TO IN THE DISCLOSURE 1
1a) D. A. Giljohann, C. A. Mirkin, Nature 2009, 462, 461-464;
1b) P. Yager, T. Edwards, E. Fu, K. Helton, K. Nelson, M. R. Tam, B. H. Weigl, Nature 2006, 442, 412-418;
1c) C. Parolo, A. Merkoci, Chem. Soc. Rev. 2013, 42, 450-457.
2
2a) A. Fire, S. Q. Xu, Proc. Natl. Acad. Sci. USA 1995, 92, 4641-4645;
2b) M. M. Ali, F. Li, Z. Zhang, K. Zhang, D. K. Kang, J. A. Ankrum, X. C. Le, W. Zhao, Chem. Soc. Rev. 2014, 43, 3324-3341;
2c) M. Liu, W. Zhang, Q. Zhang, J. D. Brennan, Y. Li, Angew. Chem. Int. Ed. 2015, 54, 9637-9641; and Angew. Chem. 2015, 127, 9773-9777;
2d) M. Liu, Q. Zhang, Z. Li, J. Gu, J. D. Brennan, Y. Li, Nat. Commun. 2016, 7, 12704;
2e) M. Liu, Q. Zhang, D. Chang, J. Gu, J. D. Brennan, Y. Li, Angew. Chem. Int. Ed. 2017, 56, 6142-6146; and Angew. Chem. 2017, 129, 6238-6242;

2f) M. Liu, Q. Zhang, B. Kannan, G. A. Botton, J. Yang, L. Soleymani, J. D. Brennan, Y. Li, Angew. Chem. Int. Ed. 2018, 57, 12440-12443; and Angew. Chem. 2018, 130, 12620-12623.

3
3a) R. R. Breaker, Nat. Biotechnol. 1997, 15, 427-431;
3b) K. Schlosser, Y. Li, Chem. Biol. 2009, 16, 311-322;
3c) S. K. Silverman, Trends Biochem. Sci. 2016, 41, 595-609;
3d) M. Liu, D. Chang, Y. Li, Acc. Chem. Res. 2017, 50, 2273-2283;
3e) D. Morrison, M. Rothenbroker, Y. Li, Small Methods 2018, 2, 1700319.

4
4a) A. D. Ellington, J. W. Szostak, Nature 1990, 346, 818-822;
4b) C. Tuerk, L. Gold, Science 1990, 249, 505-510.

5
5a) N. K. Navani, Y. Li, Curr. Opin. Chem. Biol. 2006, 10, 272-281;
5b) J. Liu, Z. Cao, Y. Lu, Chem. Rev. 2009, 109, 1948-1998;
5c) Y. Xiang, Y. Lu, Nat. Chem. 2011, 3, 697-703;
5d) K. Tram, P. Kanda, B. J. Salena, S. Huan, Y. Li, Angew. Chem. Int. Ed. 2014, 53, 12799-12802; and Angew. Chem. 2014, 126, 13013-13016;
5e) W. Zhang, Q. Feng, D. Chang, K. Tram, Y. Li, Methods 2016, 106, 66-75.

6
6a) J. Li, Y. Lu, J. Am. Chem. Soc. 2000, 122, 10466-10467;
6b) K. Hwang, P. Wu, T. Kim, L. Lei, S. Tian, Y. Wang, Y. Lu, Angew. Chem. Int. Ed. 2014, 53, 13798-13802; and Angew. Chem. 2014, 126, 14018-14022;
6c) P. J. Huang, J. Liu, Anal. Chem. 2014, 86, 5999-6005;
6d) S. He, L. Qu, Z. Shen, Y. Tan, M. Zeng, F. Liu, Y. Jiang, Y. Li, Anal. Chem. 2015, 87, 569-577;
6e) Z. Shen, Z. Wu, D. Chang, W. Zhang, K. Tram, C. Lee, P. Kim, B. J. Salena, Y. Li, Angew. Chem. Int. Ed. 2016, 55, 2431-2434; and Angew. Chem. 2016, 128, 2477-2480.

7
7a) M. M. Ali, S. D. Aguirre, H. Lazim, Y. Li, Angew. Chem. Int. Ed. 2011, 50, 3751-3754;
And Angew. Chem. 2011, 123, 3835-3838;
7b) S. D. Aguirre, M. M. Ali, B. J. Salena, Y. Li, Biomolecules 2013, 3, 563-577.

8. K. Tram, P. Kanda, B. J. Salena, S. Huan, Y. Li, Angew. Chem. Int. Ed. 2014, 53, 12799-12802.
9. D. Chang, K. Tram, B. Li, Q. Feng, Z. Shen, C. H. Li, B. J. Salena, Y. Li, Sci. Rep. 2017, 7, 31.
10. W. M. Deen, Introduction to Chemical Engineering Fluid Mechanics, Cambridge University Press, 2016.
11. S. D1. Aguirre, M. M. Ali, B. J. Salena, Y. Li, Biomolecules 2013, 3, 563-577.
12. M. Liu, Q. Zhang, Z. Li, J. Gu, J. D. Brennan, Y. Li, Nat. Commun. 2016, 7, 12074.
13. M. Liu, Q. Zhang, D. Chang, J. Gu, J. D. Brennan, Y. Li, Angew. Chem. Int. Ed. 2017, 56, 6142-6146.
14. M. Liu, Q. Zhang, J. D. Brennan, Y. Li, MRS Commun. 2018, 8, 687-694.
15. M. Liu, Q. Zhang, B. Kannan, G. A. Botton, J. Yang, L. Soleymani, J. D. Brennan, Y. Li, Angew. Chem. Int. Ed. 2018, 57, 12440-12443.
16. M. M. Ali, C. L. Brown, S. Jahanshahi-Anbuhi, B. Kannan, Y. Li, C. D. M. Filipe, J. D. Brennan, Sci. Rep. 2017, 7, 12335.
17. P. Dua, S. Ren, S. W. Lee, J.-K. Kim, H.-S. Shin, O.-C. Jeong, S. Kim, D.-K. Lee, Mol. Cells 2016, 39, 807-813.
18. W. Wu, J. Zhang, M. Zheng, Y. Zhong, J. Yang, Y. Zhao, W. Wu, W. Ye, J. Wen, Q. Wang, et al., PLoS One 2012, 7, e48999.
19. X. Yu, F. Chen, R. Wang, Y. Li, J. Biotechnol. 2018, 266, 39-49.
20. J. Meng, S. Zhao, M. P. Doyle, S. E. Mitchell, S. Kresovich, Int. J. Food Microbiol. 1996, 32, 103-113.
21. A. M. Ibekwe, P. M. Watt, C. M. Grieve, V. K. Sharma, S. R. Lyons, Appl. Environ. Microbiol. 2002, 68, 4853-4862.
22. J. Waswa, J. Irudayaraj, C. DebRoy, LWT—Food Sci. Technol. 2007, 40, 187-192.
23. N. Adányi, M. Váradi, N. Kim, I. Szendrö, in Curr. Appl. Phys. 2006, pp. 279-286.
24. N. J. C. Strachan, I. D. Ogden, FEMS Microbiol. Lett. 2000, 186, 79-84.
25. B. Thakur, G. Zhou, J. Chang, H. Pu, B. Jin, X. Sui, X. Yuan, C. H. Yang, M. Magruder, J. Chen, Biosens. Bioelectron. 2018, 110, 16-22.
26. M. M. Ali, A. Slepenkin, E. Peterson, W. Zhao, ChemBioChem 2019, 20, 906-910. 26

27a) D. Chang, K. Tram, B. Li, Q. Feng, Z. Shen, C. H. Li, B. J. Salena, Y. Li, Sci. Rep. 2017, 7, 3110;
27b) S. Manochehry, E. M. McConnell, K. Q. Tram, J. Macri, Y. Li, Front. Chem. 2018, 6, 332.

28. M. M. Ali, C. L. Brown, S. Jahanshahi-Anbouhi, B. Kannan, Y. Li, C. D. M. Filipe, J. D. Brennan, Sci. Rep. 2017, 7, 12335.

29
29a) J. Li, W. Zheng, A. H. Kwon, Y. Lu, Nucleic Acids Res. 2000, 28, 481-488;
29b) Z. Liu, S. H. J. Mei, J. D. Brennan, Y. Li, J. Am. Chem. Soc. 2003, 125, 7539-7545;
29c) A. K. Brown, J. Li, C. M. B. Pavot, Y. Lu, Biochemistry 2003, 42, 7152-7161;
29d) S. F. Torabi, P. Wu, C. E. McGhee, L. Chen, K. Hwang, N. Zheng, J. Cheng, Y. Lu, Proc. Natl. Acad. Sci. USA 2015, 112, 5903-5908;
29e) K. Tram, J. Xia, R. Gysbers, Y. Li, PLoS One 2015, 10, e0126402;
29f) R. Saran, J. Liu, Anal. Chem. 2016, 88, 4014-4020.

The invention claimed is:

1. A biosensor for detection of an analyte comprising:
a) i) a nucleic acid substrate coupled to a first support and a nucleic acid cleaving enzyme; or
ii) a nucleic acid cleaving enzyme comprising a nucleic acid substrate coupled to a first support; and
b) a nucleic acid binding molecule coupled to a microzone on a second support;
wherein the nucleic acid substrate comprises a detection moiety;
wherein the nucleic acid enzyme is configured for cleaving the nucleic acid substrate;
wherein the nucleic acid cleaving enzyme is configured to be activated upon contact with the analyte, and the activated nucleic acid cleaving enzyme is configured for cleaving the nucleic acid substrate to release a cleavage product comprising the detection moiety;
wherein the nucleic acid binding molecule is configured for binding to the cleavage product,
wherein the nucleic acid substrate coupled to the first support or the nucleic acid cleaving enzyme comprising a nucleic acid substrate coupled to the first support, and the nucleic acid binding molecule coupled to a microzone on the second support, are configured for use in a container, optionally a test tube, and
wherein the biosensor is configured to be used with a test solution of up to about 100 mL comprising the analyte.

2. The biosensor of claim 1, wherein the nucleic acid cleaving enzyme is an RNA-cleaving DNAzyme, a DNA-cleaving DNAzyme, a ribozyme, or an endonuclease.

3. The biosensor of claim 2, wherein the nucleic acid cleaving enzyme is an RNA-cleaving DNAzyme and the nucleic acid binding molecule is an oligonucleotide.

4. The biosensor of claim 1, wherein the first support comprises modified agarose beads, graphene oxide, gold nanoparticles or glass beads, and wherein the nucleic acid cleaving enzyme is coupled to the first support by covalent or non-covalent immobilization chemistry.

5. The biosensor of claim 4, wherein the immobilization chemistry comprises streptavidin, cyanuric chloride, isothiocyanate, nitrophenyl chloroformate, hydrazine, amino, thiol, acrydite, NHS ester activated, aldehyde, azlactone-activated, carbonyl diimidazole activated, maleimide, iodo-acetyl-activated, or biotin chemistries.

6. The biosensor of claim 1, wherein the second support comprises paper or a paper-based product, glass fiber substrate, graphene paper, modified agarose beads, graphene oxide, gold nanoparticles, or glass beads.

7. The biosensor of claim 1, wherein the microzone comprises hydrophobic material.

8. The biosensor of claim 1, wherein the nucleic acid binding molecule is conjugated to biotin and the second support is conjugated to streptavidin, and wherein the biotin is bound to the streptavidin.

9. The biosensor of claim 1, wherein the detection moiety comprises a fluorescent, colorimetric, chemiluminescent, or electrochemical detection moiety.

10. The biosensor of claim 9, wherein the fluorescent detection moiety is a fluorescein dye, cyanine dye, rhodamine dye, TYE™ dye, ATTO™ dye, Alexa Fluor® dye, or LI-COR IRDye®.

11. The biosensor of claim 9, wherein the colorimetric detection moiety comprises an enzymatic moiety, and wherein the enzymatic moiety comprises urease, alkaline phosphatase, horseradish peroxidase, glucose oxidase, or β-galactosidase.

12. The biosensor of claim 1, further comprising;
  i) one or more additional nucleic acid substrates coupled to the first support and one or more additional nucleic acid cleaving enzymes, or
  ii) one or more additional nucleic acid cleaving enzymes each comprising one of one or more additional nucleic acid substrates coupled to the first support,
  wherein each of the one or more additional nucleic acid substrates comprises a detection moiety;
  wherein each of the one or more additional nucleic acid cleaving enzyme is configured to be activated upon contact with one of one or more additional analytes, and the activated additional nucleic acid cleaving enzyme is configured for cleaving the one or more additional nucleic acid substrates to release one or more additional cleavage products each comprising a detection moiety;
  wherein each of the one or more additional nucleic acid cleaving enzyme is specific to one of the one or more additional analytes;
  wherein the biosensor further comprises one or more additional nucleic acid binding molecules, each of the one or more additional nucleic acid binding molecule is configured for binding to one of the one or more additional cleavage products; and
  wherein each of the one or more additional nucleic acid binding molecules is concentrated within one of one or more additional microzones on the second support.

13. A method for the detection of at least one analyte in a sample, the method comprising:
  a) placing the biosensor of claim 1 into a test solution comprising the sample;
  b) retrieving the second support from the test solution; and
  c) detecting the presence of the at least one analyte on the second support.

14. The method of claim 13, further comprising after step b), washing the second support.

15. The method of claim 13, wherein the biosensor further comprises i) one or more additional nucleic acid substrates coupled to the first support and one or more additional nucleic acid cleaving enzymes, or ii) one or more additional nucleic acid cleaving enzymes each comprising one of one or more additional nucleic acid substrates, and one or more additional nucleic acid binding molecules.

16. The method of claim 13, wherein the test solution is up to about 100 mL.

17. A kit for detecting an analyte, wherein the kit comprises the biosensor of claim 1, and instructions for use of the kit for detecting an analyte.

18. The kit of claim 17, further comprising one or more of a) to g): a) a container, b) a buffer, c) a washing solution, d) a detection system comprising i) a substrate for an enzymatic moiety, ii) a substrate for chemiluminescent detection, and/or iii) a color changing dye, e) one or more additional nucleic acid substrates coupled to the first support, f) one or more additional nucleic acid cleaving enzymes each configured to be activated by one of one or more additional analytes coupled to the first support, and g) one or more additional nucleic acid binding molecules coupled to the second support.

19. The biosensor of claim 1, further comprising a container, optionally a test tube.

* * * * *